(12) United States Patent
Miyazawa et al.

(10) Patent No.: US 11,529,126 B2
(45) Date of Patent: Dec. 20, 2022

(54) ULTRASONIC DEVICE, ULTRASONIC MODULE, AND ULTRASONIC MEASURING APPARATUS

(71) Applicant: Seiko Epson Corporation, Tokyo (JP)

(72) Inventors: Hiromu Miyazawa, Azumino (JP); Hiroshi Ito, Suwa (JP); Tomoaki Nakamura, Chino (JP); Masayoshi Yamada, Chino (JP); Kanechika Kiyose, Matsumoto (JP); Tsukasa Funasaka, Shiojiri (JP)

(73) Assignee: SEIKO EPSON CORPORATION

( * ) Notice: Subject to any disclaimer, the term of this patent is extended or adjusted under 35 U.S.C. 154(b) by 1076 days.

(21) Appl. No.: 16/097,113

(22) PCT Filed: Apr. 18, 2017

(86) PCT No.: PCT/JP2017/015635
§ 371 (c)(1),
(2) Date: Oct. 26, 2018

(87) PCT Pub. No.: WO2017/188072
PCT Pub. Date: Nov. 2, 2017

(65) Prior Publication Data
US 2019/0343492 A1 Nov. 14, 2019

(30) Foreign Application Priority Data
Apr. 28, 2016 (JP) .............................. JP2016-090953

(51) Int. Cl.
*B06B 1/06* (2006.01)
*A61B 8/00* (2006.01)
(Continued)

(52) U.S. Cl.
CPC .................. *A61B 8/54* (2013.01); *A61B 8/13* (2013.01); *B06B 1/0215* (2013.01);
(Continued)

(58) Field of Classification Search
CPC ... B06B 1/0215; B06B 1/0622; H01L 41/042; H01L 41/053; H01L 41/0825
(Continued)

(56) References Cited

U.S. PATENT DOCUMENTS

2002/0105250 A1 8/2002 Klee et al.
2012/0319529 A1 12/2012 Nakazawa et al.
(Continued)

FOREIGN PATENT DOCUMENTS

JP H04-149078 A 5/1992
JP H09-033498 A 2/1997
(Continued)

*Primary Examiner* — Derek J Rosenau
(74) *Attorney, Agent, or Firm* — Harness, Dickey & Pierce, P.L.C.

(57) ABSTRACT

An ultrasonic device includes: a substrate provided with a first opening and a second opening; a support film that is provided on the substrate and blocks the first opening and the second opening; a transmitting piezoelectric film that is provided on the support film at a position which overlaps the first opening when viewed in a thickness direction of the substrate and is interposed between a pair of electrodes in the thickness direction of the substrate; and a receiving piezoelectric film that is provided on the support film at a position which overlaps the second opening when viewed in the thickness direction of the substrate and is interposed between a pair of electrodes in the thickness direction of the substrate. In the thickness direction of the substrate, a thickness dimension of the transmitting piezoelectric film is smaller than a thickness dimension of the receiving piezoelectric film.

8 Claims, 16 Drawing Sheets

(51) Int. Cl.
  *A61B 8/13* (2006.01)
  *B06B 1/02* (2006.01)
  *H01L 41/04* (2006.01)
  *H01L 41/053* (2006.01)
  *H01L 41/08* (2006.01)
  *H04R 17/00* (2006.01)

(52) U.S. Cl.
  CPC .......... B06B 1/0622 (2013.01); H01L 41/042 (2013.01); H01L 41/053 (2013.01); H01L 41/0825 (2013.01); H04R 17/00 (2013.01); *B06B 2201/76* (2013.01)

(58) Field of Classification Search
  USPC ........................................ 310/322, 334, 335
  See application file for complete search history.

(56) References Cited

U.S. PATENT DOCUMENTS

2015/0105663 A1* 4/2015 Kiyose .................... B06B 1/067
  29/25.35
2015/0187347 A1* 7/2015 Kojima ............... H01L 41/0973
  310/322

FOREIGN PATENT DOCUMENTS

| JP | 2002-271897 A | 9/2002 |
| JP | 2010-147658 A | 7/2010 |
| JP | 2013-005137 A | 1/2013 |
| JP | 2015-076825 A | 4/2015 |
| WO | WO-2016-002971 A1 | 1/2016 |

* cited by examiner

ULTRASONIC DEVICE, ULTRASONIC MODULE, AND ULTRASONIC MEASURING APPARATUS

CROSS-REFERENCE TO RELATED APPLICATIONS

This application is a U.S. National Stage Application of International Application No. PCT/JP2017/015635, filed on Apr. 18, 2017, and published in Japanese as WO 2017/188072 A1 on Nov. 2, 2017, which claims priority to Japanese Patent Application No. 2016-090953, filed on Apr. 28, 2016. The entire disclosures of the above applications are incorporated herein by reference.

BACKGROUND

Technical Field

The present invention relates to an ultrasonic device, an ultrasonic module, and an ultrasonic measuring apparatus.

Related Art

In the related art, an ultrasonic transducer using a so-called bulk-type piezoelectric body has been known as an ultrasonic transducer that performs a transmitting process and a receiving process of an ultrasonic wave, the ultrasonic transducer including a piezoelectric body interposed between a pair of electrodes, transmitting the ultrasonic wave by applying a voltage between the electrodes and causing the piezoelectric body to vibrate, and receiving the ultrasonic wave by detecting an output voltage from the piezoelectric body to which the ultrasonic wave is input.

However, the bulk-type piezoelectric body needs to have a large thickness dimension, and thus it is difficult to achieve a thin or compact piezoelectric body.

In this respect, there has been known an ultrasonic transducer using a thin piezoelectric film, the ultrasonic transducer being configured to include a vibration film provided to cover an opening of a support body provided with the opening and the piezoelectric film that is provided on the vibration film and is interposed between a pair of electrodes (for example, refer to JP-2002-271897).

The ultrasonic transducer causes the vibration film to vibrate by applying the voltage between the electrodes so as to transmit the ultrasonic wave and detects reception of the ultrasonic wave in response to an output voltage from the piezoelectric film due to the vibration of the vibration film. In the ultrasonic transducer that causes the vibration film to vibrate by the thin piezoelectric body, it is possible to significantly reduce a thickness dimension thereof in an ultrasonic-wave transmitting/receiving direction, compared to the bulk-type ultrasonic transducer, and thus it is possible to obtain a thin or compact ultrasonic measuring apparatus.

Incidentally, the thin-film type ultrasonic transducer transmits the ultrasonic wave due to the vibration of the vibration film and, then, detects reception of the ultrasonic wave from a strain of the piezoelectric film by the vibration film that is caused to vibrate in response to a reflected ultrasonic wave. In this case, when the ultrasonic wave is transmitted, the vibration film is significantly displaced, and thereby an ultrasonic wave having a high output is output. When the ultrasonic wave is received, it is necessary to detect vibration with high sensitivity so as to detect the reception of the ultrasonic wave even in a case of small vibration of the vibration film. Hence, in order to achieve characteristics depending on respective functions, it is necessary to configure an ultrasonic transducer for transmission and an ultrasonic transducer for reception. Hence, when the ultrasonic transducer disclosed in JP-2002-271897 is an ultrasonic transducer for both of transmission and reception or ultrasonic transducers having the same configuration for both of transmission and reception is used, a problem arises in that transmission and reception efficiency of the ultrasonic wave is reduced.

According to the invention, an object thereof is to provide an ultrasonic device, an ultrasonic module, and an ultrasonic measuring apparatus which have high transmission and reception efficiency of an ultrasonic wave. Hereinafter, application examples and embodiments that can achieve the object will be described.

SUMMARY

An ultrasonic device according to an application example includes: a substrate provided with a first opening and a second opening; a support film that is provided on the substrate and blocks the first opening and the second opening; a transmitting piezoelectric film that is provided on the support film at a position which overlaps the first opening when viewed in a thickness direction of the substrate and is interposed between a pair of electrodes in the thickness direction of the substrate; and a receiving piezoelectric film that is provided on the support film at a position which overlaps the second opening when viewed in the thickness direction of the substrate and is interposed between a pair of electrodes in the thickness direction of the substrate. In the thickness direction of the substrate, a thickness dimension of the transmitting piezoelectric film is smaller than a thickness dimension of the receiving piezoelectric film.

In the application example, the ultrasonic device includes an ultrasonic transducer for transmission (transmission transducer) and an ultrasonic transducer for reception (reception transducer). The transmission transducer includes the support film (a first vibration portion which is a region of the support film which overlaps the first opening), which covers the first opening of the substrate, and the transmitting piezoelectric film. The reception transducer includes the support film (a second vibration portion which is a region of the support film which overlaps the second opening), which covers the second opening of the substrate, and the receiving piezoelectric film. The transmitting piezoelectric film is formed to have a film thickness smaller than that of the receiving piezoelectric film.

In such a configuration, since the transmission transducer and the reception transducer are separately provided, it is possible to have characteristics suitable for transmitting the ultrasonic wave in the transmission transducer and to have characteristics suitable for receiving the ultrasonic wave in the reception transducer. Accordingly, it is possible to more improve transmission and reception efficiency of the ultrasonic wave, compared to a case where the transmission and the reception of the ultrasonic wave are performed in one ultrasonic transducer. In other words, it is possible to transmit an ultrasonic wave having a high acoustic pressure in the transmission of the ultrasonic wave, and it is possible to receive the ultrasonic wave with high receiving sensitivity and high accuracy in the reception of the ultrasonic wave.

Incidentally, in the transmission transducer, the first vibration portion needs to be significantly displaced with a low drive voltage, and it is necessary to output the ultrasonic wave having a high acoustic pressure. When $t_A$ represents the thickness dimension of the transmitting piezoelectric film, $V_1$ represents a drive voltage that is applied between the electrodes, c represents a dielectric constant of permittivity (the transmitting piezoelectric film) between the electrodes, and e represents a piezoelectric constant of the transmitting piezoelectric film, a strain amount η of the transmitting piezoelectric film is approximately calculated in a relationship of $\eta = \varepsilon V_1 / t_A e$. Accordingly, in order to transmit the ultrasonic wave having the high acoustic pressure by increasing the strain amount η of the transmitting piezoelectric film, it is necessary to decrease the thickness dimension $t_A$ of the transmitting piezoelectric film. Furthermore, when the thickness dimension of the transmitting piezoelectric film increases, the stiffness of the first vibration portion increases, and thus the first vibration portion is not easily bent. In this respect, it is preferable that the transmitting piezoelectric film is decreased in the thickness dimension.

On the other hand, in the transmission transducer, the ultrasonic wave is transmitted, and then the reflected ultrasonic wave is received. There is a high possibility that the reflected ultrasonic wave is significantly attenuated more than the ultrasonic wave transmitted from the transmission transducer, and thus the displacement of the second vibration portion also decreases in some cases. Even in this case, the reception transducer needs to detect the vibration of the second vibration portion in response to the reflected ultrasonic wave with high sensitivity. When η represents a displacement amount (strain amount) of the receiving piezoelectric film due to the vibration of the second vibration portion, $t_B$ represents a thickness dimension of the receiving piezoelectric film (a distance between electrodes), ε represents a dielectric constant of a permittivity (the transmitting piezoelectric film) between the electrodes, and e represents a piezoelectric constant of the receiving piezoelectric film, an output voltage $V_2$ that is output from the electrode in the reception transducer is approximately calculated in a relationship of $V_2 = \eta t_B e / \varepsilon$. Accordingly, in order to increase the output voltage $V_2$ from the receiving piezoelectric film, it is necessary to increase the thickness dimension of the receiving piezoelectric film.

In the application example, the transmitting piezoelectric film is configured to have a thickness dimension smaller than the thickness dimension of the receiving piezoelectric film. In other words, compared to a case where the transmission and the reception of the ultrasonic wave is performed by one ultrasonic transducer, a case where the transmission transducer and the reception transducer are each configured to use the piezoelectric film having the same thickness dimension, or the like, it is possible for the transmission transducer to have higher transmission efficiency of the ultrasonic wave, and it is possible for the reception transducer to have higher reception efficiency of the ultrasonic wave.

In the ultrasonic device according to the application example, the thickness dimension of the transmitting piezoelectric film is 300 nm or larger and 2,750 nm or smaller, the thickness dimension of the receiving piezoelectric film is 600 nm or larger and 3,100 nm or smaller, and a difference between the thickness dimensions of the transmitting piezoelectric film and the receiving piezoelectric film is 350 nm or larger.

In the application example, the transmitting piezoelectric film has the thickness dimension of 300 nm or larger and 2,750 nm or smaller, and the receiving piezoelectric film has the thickness dimension of 600 nm or larger and 3,100 nm or smaller. The transmitting piezoelectric film is formed to be thinner than the receiving piezoelectric film by 350 nm or larger. In such a configuration, it is possible to improve the transmission efficiency of the ultrasonic wave of the transmitting piezoelectric film, and it is possible to improve the reception efficiency of the ultrasonic wave of the receiving piezoelectric film.

In addition, when a product of a strain amount (nm) of the first vibration portion obtained when a predetermined voltage is applied to the transmission transducer and receiving sensitivity (nV/Pa) in the reception transducer is defined as a figure of merit (nm·nV/Pa) of transmission and reception of the ultrasonic wave in the ultrasonic device, it is preferable that the figure of merit is higher than 75,000 (nm·nV/Pa). Such configurations of the transmitting piezoelectric film and the receiving piezoelectric film as described above make it possible to obtain a sufficient figure of merit regardless of opening widths (opening areas) of the first opening and the second opening, and thus it is possible to obtain the ultrasonic device having the high transmission and reception efficiency.

In the ultrasonic device according to the application example, it is preferable that an opening width of the first opening is smaller than an opening width of the second opening.

In the application example, the opening width (opening area) of the first opening is smaller than the opening width (opening area) of the second opening. In other words, an area of the first vibration portion constituting the transmission transducer is smaller than the area of the second vibration portion constituting the reception transducer.

In the ultrasonic transducer in which the vibration portion is formed by the support film that blocks the opening and the piezoelectric film that is interposed between the pair of electrodes is disposed on the vibration portion, a frequency of the ultrasonic wave which is transmitted and received (the natural frequency of the ultrasonic transducer) depends on the opening width of the opening (the area of the vibration portion) and the thickness dimension of the piezoelectric film. The natural frequency of the ultrasonic transducer decreases as the opening width of the opening increases, and the natural frequency decreases as the thickness dimension of the piezoelectric film decreases. As described above, in the application example, the transmitting piezoelectric film has the thickness dimension smaller than the thickness dimension of the receiving piezoelectric film. Hence, the opening width of the first opening is smaller than the opening width of the second opening, and thereby the frequency of the ultrasonic wave that is transmitted from the transmission transducer can be substantially equal to the frequency of the ultrasonic wave that is received by the reception transducer.

In the ultrasonic device according to the application example, it is preferable that the support film is provided with a first vibration portion that blocks the first opening and a second vibration portion that blocks the second opening, a transmission transducer is configured to have the first vibration portion and the transmitting piezoelectric film, a reception transducer is configured to have the second vibration portion and the receiving piezoelectric film, and a natural frequency of the transmission transducer is different from a natural frequency of the reception transducer.

In the application example, the transmission transducer and the reception transducer have different natural frequencies from each other. As described above, in the application example, the ultrasonic wave is transmitted from the transmission transducer, and the reception transducer receives an ultrasonic wave reflected from a target subject; however, in this case, when the natural frequencies of the transmission transducer and the reception transducer are caused to be equal to each other, and the ultrasonic wave is transmitted from the transmission transducer, the reception transducer is likely to resonate. In this case, an output voltage containing a noise component is output from the reception transducer and influences reception accuracy of the ultrasonic wave. In this respect, in the application example, since the natural frequencies of the transmission transducer and the reception transducer are different from each other, it is possible to suppress the resonance of the reception transducer when the ultrasonic wave is received, and thus it is possible to suppress a defect due to noise contained in the output voltage.

In the ultrasonic device according to the application example, it is preferable that a difference between the natural frequency of the transmission transducer and the natural frequency of the reception transducer is 0.2 MHz or higher and 0.8 MHz or lower.

In a case where a difference between the natural frequencies of the transmission transducer and the reception transducer is smaller than 0.2 MHz, as described above, the reception transducer resonates when the ultrasonic wave is transmitted, and thereby a large amount of noise is contained in the output voltage. Thus, the reception accuracy decreases in the reception accuracy. On the other hand, in a case where a difference between the natural frequencies of the transmission transducer and the reception transducer exceeds 0.8 MHz, a difference between the frequency of the ultrasonic wave transmitted from the transmission transducer and the frequency of the ultrasonic wave that is suitable to be received by the reception transducer increases, and thus the reception accuracy decreases in the reception transducer.

In this respect, in the application example, the difference between the natural frequencies of the transmission transducer and the reception transducer is 0.2 MHz or higher and 0.8 MHz or lower. In this manner, while the noise component is reduced, it is possible for the reception transducer to receive, with high receiving sensitivity, a reflected wave of the ultrasonic wave transmitted from the transmission transducer, and improvement in the transmission and reception efficiency of the ultrasonic wave is achieved in the ultrasonic device.

In the ultrasonic device according to the application example, it is preferable that the natural frequency of the reception transducer is lower than the natural frequency of the transmission transducer.

In the application example, the natural frequency of the reception transducer is lower than the natural frequency of the transmission transducer. In other words, in a case where the transmission transducer transmits the ultrasonic wave and the reception transducer receives the ultrasonic wave reflected from the target subject, the reflected ultrasonic wave is significantly attenuated more than the transmitted ultrasonic wave. Hence, in the ultrasonic measurement, it is necessary to increase the receiving sensitivity in the reception transducer. In the application example, the natural frequency of the reception transducer is decreased, that is, the opening width of the second opening is increased. Consequently, the second vibration portion in the reception transducer is easily bent, and thus it is possible to increase the receiving sensitivity.

Even when the receiving piezoelectric film has a small thickness dimension, it is possible to decrease the natural frequency; however, in this case, the receiving sensitivity of the reception transducer decreases, and thus the figure of merit of transmission and reception is considered to decrease in the ultrasonic device. Hence, it is preferable that the opening width of the second opening is widened.

It is preferable that the ultrasonic device according to the application example further includes a polarization voltage output unit that applies a transmission polarization voltage to the transmitting piezoelectric film and applies a reception polarization voltage to the receiving piezoelectric film, and the transmission polarization voltage is lower than the reception polarization voltage.

In the application example, the polarization voltage output unit that applies the polarization voltage to the ultrasonic device is provided. In a case of performing ultrasonic measurement in the ultrasonic device, the polarization voltage is applied to the transmitting piezoelectric film and the receiving piezoelectric film from the polarization voltage output unit such that polarization is performed before a transmission/reception process is performed, and thereby improvement in the transmission and reception efficiency is achieved in the ultrasonic device. In this case, the polarization voltage output unit makes a transmission polarization voltage to the transmitting piezoelectric film having the smaller thickness dimension smaller than a reception polarization voltage to the receiving piezoelectric film having the larger thickness dimension. Consequently, it is possible to suppress dielectric breakdown in the transmitting piezoelectric film, and thus it is possible to appropriately polarize the piezoelectric films.

An ultrasonic module according to an application example includes: an ultrasonic device including a substrate provided with a first opening and a second opening, a support film that is provided on the substrate and blocks the first opening and the second opening, a transmitting piezoelectric film that is provided on the support film at a position which overlaps the first opening when viewed in a thickness direction of the substrate and is interposed between a pair of electrodes in the thickness direction of the substrate, and a receiving piezoelectric film that is provided on the support film at a position which overlaps the second opening when viewed in the thickness direction of the substrate and is interposed between a pair of electrodes in the thickness direction of the substrate; and a case that stores the ultrasonic device. In the thickness direction of the substrate, a thickness dimension of the transmitting piezoelectric film is smaller than a thickness dimension of the receiving piezoelectric film.

In the application example, as described above, it is possible to improve the transmission and reception efficiency in the ultrasonic device. Hence, it is possible to achieve the same operational effects also in the ultrasonic module that stores the ultrasonic device, and thus it is possible to improve the transmission and reception efficiency when a transmission/reception process of the ultrasonic wave is performed.

An ultrasonic measuring apparatus according to an application example includes: an ultrasonic device that including a substrate provided with a first opening and a second opening, a transmitting piezoelectric film that is provided on a support film at a position which overlaps the first opening when viewed in a thickness direction of the substrate and is interposed between a pair of electrodes in the thickness direction of the substrate, and a receiving piezoelectric film that is provided on the support film at a position which overlaps the second opening when viewed in the thickness direction of the substrate and is interposed between a pair of electrodes in the thickness direction of the substrate; and a controller that controls the ultrasonic device. In the thickness direction of the substrate, a thickness dimension of the transmitting piezoelectric film is smaller than a thickness dimension of the receiving piezoelectric film.

In the application example, as described above, it is possible to improve the transmission and reception efficiency in the ultrasonic device. Hence, the controller controls the ultrasonic device, and thereby, through the transmission/reception process of the ultrasonic wave, which has high transmission and reception efficiency, it is possible to realize the ultrasonic measurement with high accuracy. For example, in a case of acquiring an internal tomographic image of the target subject based on measurement results of the ultrasonic measurement, it is possible to acquire the internal tomographic image with high accuracy.

DETAILED DESCRIPTION

Figure 1:
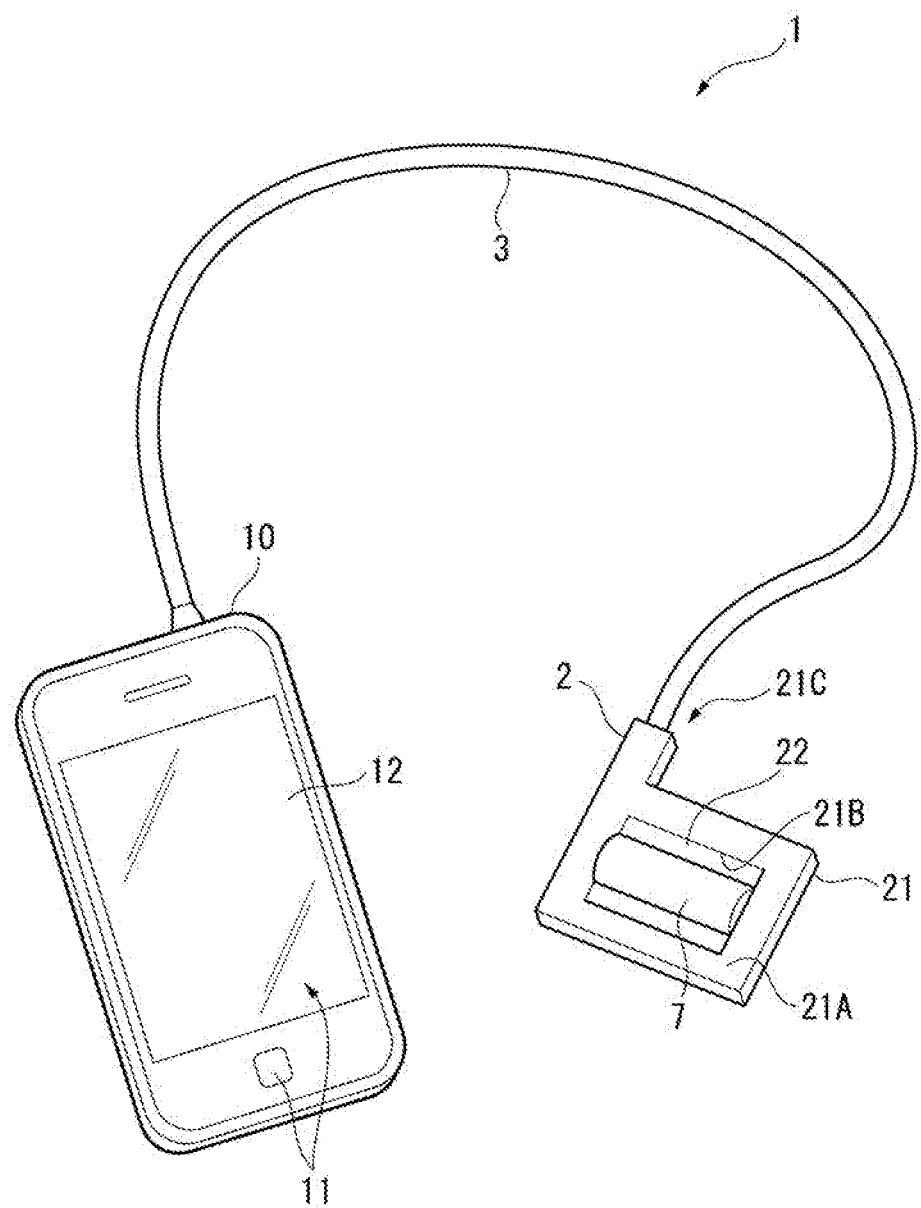
FIG. 1 is a perspective view showing a schematic configuration of an ultrasonic measuring apparatus according to a first embodiment of the invention.
Figure 2:
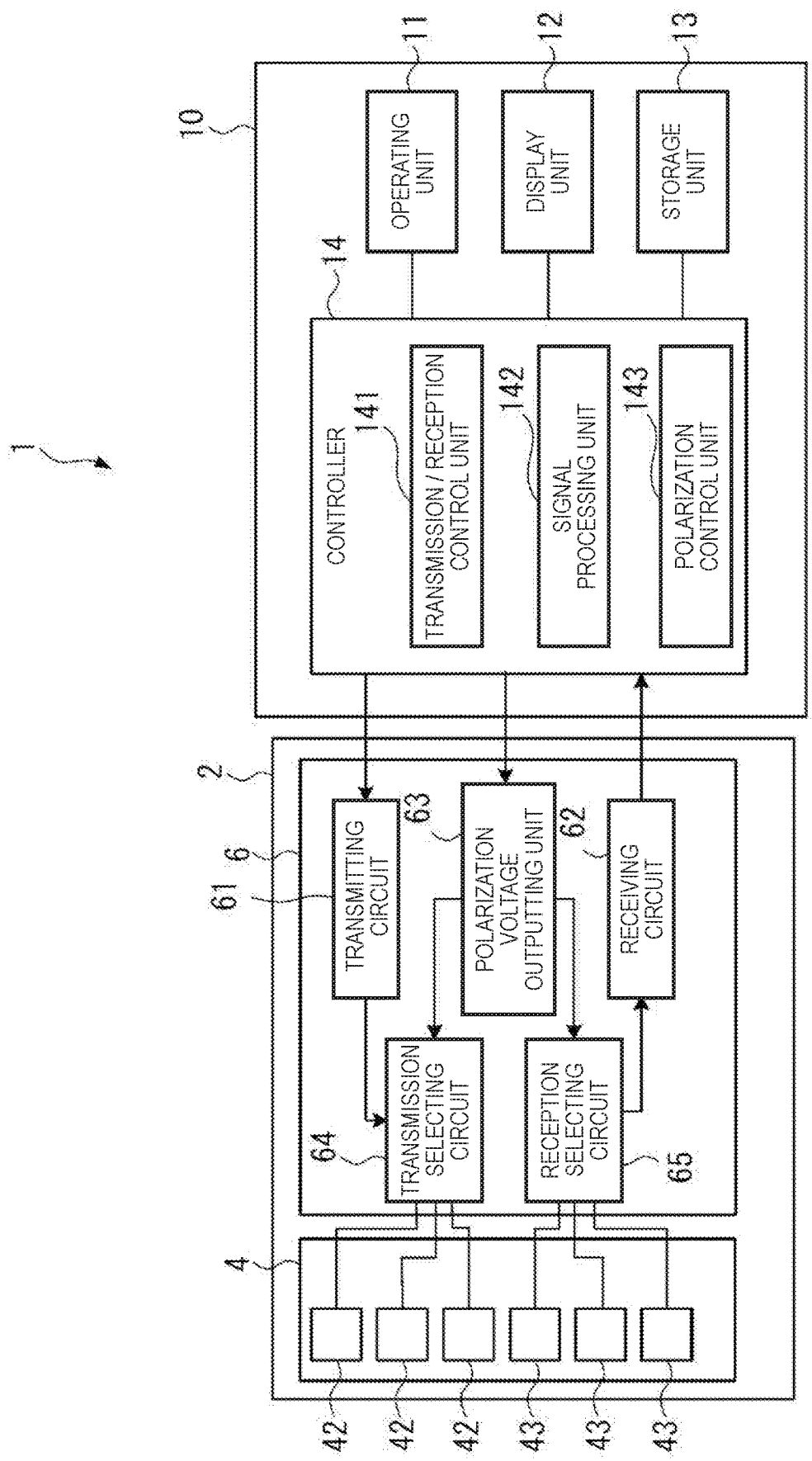
FIG. 2 is a block diagram showing a schematic configuration of the ultrasonic measuring apparatus according to the first embodiment.

Hereinafter, an ultrasonic measuring apparatus of this embodiment will be described with reference to the figures.
Configuration of Ultrasonic Measuring Apparatus FIG. 1 is a perspective view showing a schematic configuration of an ultrasonic measuring apparatus 1 according to the embodiment. FIG. 2 is a block diagram showing a schematic configuration of the ultrasonic measuring apparatus 1 of the embodiment.

As shown in FIG. 1, the ultrasonic measuring apparatus 1 of the embodiment includes an ultrasonic probe 2 and a control device 10 that is electrically connected to the ultrasonic probe 2 via a cable 3.

Figure 3:
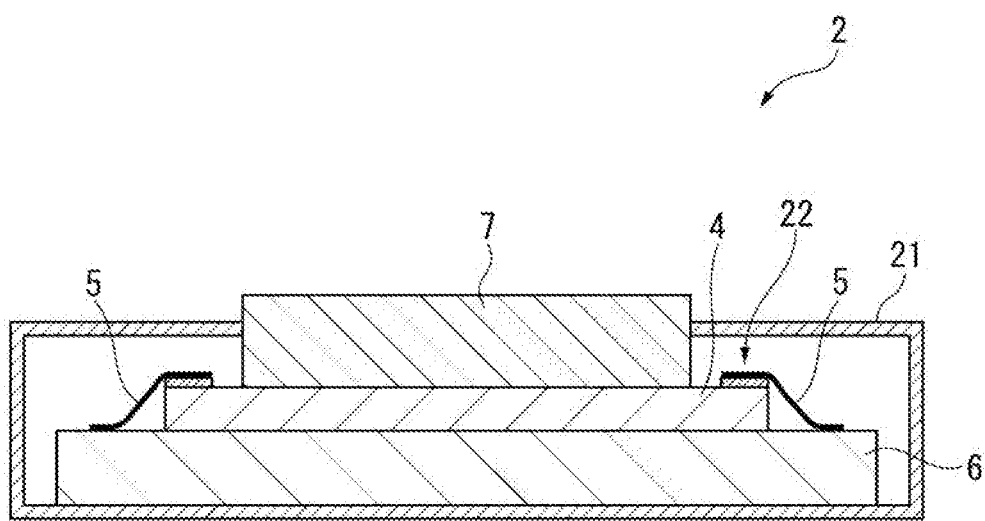
FIG. 3 is a sectional view showing a schematic configuration of an ultrasonic probe of the first embodiment.

In the ultrasonic measuring apparatus 1, the ultrasonic probe 2 comes into contact with a surface of a target subject (for example, a living body), and an ultrasonic wave is transmitted into the living body from the ultrasonic probe 2. In addition, the ultrasonic wave reflected from an organ in the target subject (living body) is received by the ultrasonic probe 2 and, for example, an internal tomographic image of the inside of the living body is acquired, based on a receiving signal thereof, or a state (for example, bloodstream or the like) of the organ in the living body is measured.
Configuration of Ultrasonic Probe FIG. 3 is a sectional view showing a schematic configuration of the ultrasonic probe 2.

The ultrasonic probe 2 is an ultrasonic module and includes a case 21 and an ultrasonic sensor 22.
Configuration of Case As shown in FIG. 1, the case 21 is formed to have a box shape with a rectangular shape in plan view, and stores the ultrasonic sensor 22. One surface (sensor surface 21A) orthogonal to a thickness direction of the case 21 is provided with a sensor window 21B through which a part (acoustic lens 7 which will be described below) of the ultrasonic sensor 22 is exposed. In addition, a part (side surface in an example shown in FIG. 1) of the case 21 is provided with a passing hole, and the cable 3 is inserted into the case 21 via the passing hole. Although not shown, the cable 3 is connected to the ultrasonic sensor 22 (circuit substrate 6 which will be described below) inside the case 21.

In the embodiment, a configuration example in which the ultrasonic probe 2 and the control device 10 are connected to each other via the cable 3 is described, but, this is only an example, and, for example, the ultrasonic probe 2 and the control device 10 may be connected to each other through wireless communication, and various constituent elements of the control device 10 may be provided in the ultrasonic probe 2.
Configuration of Ultrasonic Sensor As shown in FIG. 3, the ultrasonic sensor 22 includes an ultrasonic device 4, the circuit substrate 6, and the acoustic lens 7. As will be described below, the circuit substrate 6 is provided with a driver circuit or the like for controlling the ultrasonic device 4, and the ultrasonic device 4 is electrically connected to the circuit substrate 6 via a wiring member 5 such as a flexible substrate, for example. A surface of the ultrasonic device 4 on an ultrasonic transmission and reception side is provided with the acoustic lens 7, and the acoustic lens 7 is exposed outside from one surface side of the case 21.

Configuration of Ultrasonic Device

Figure 4:
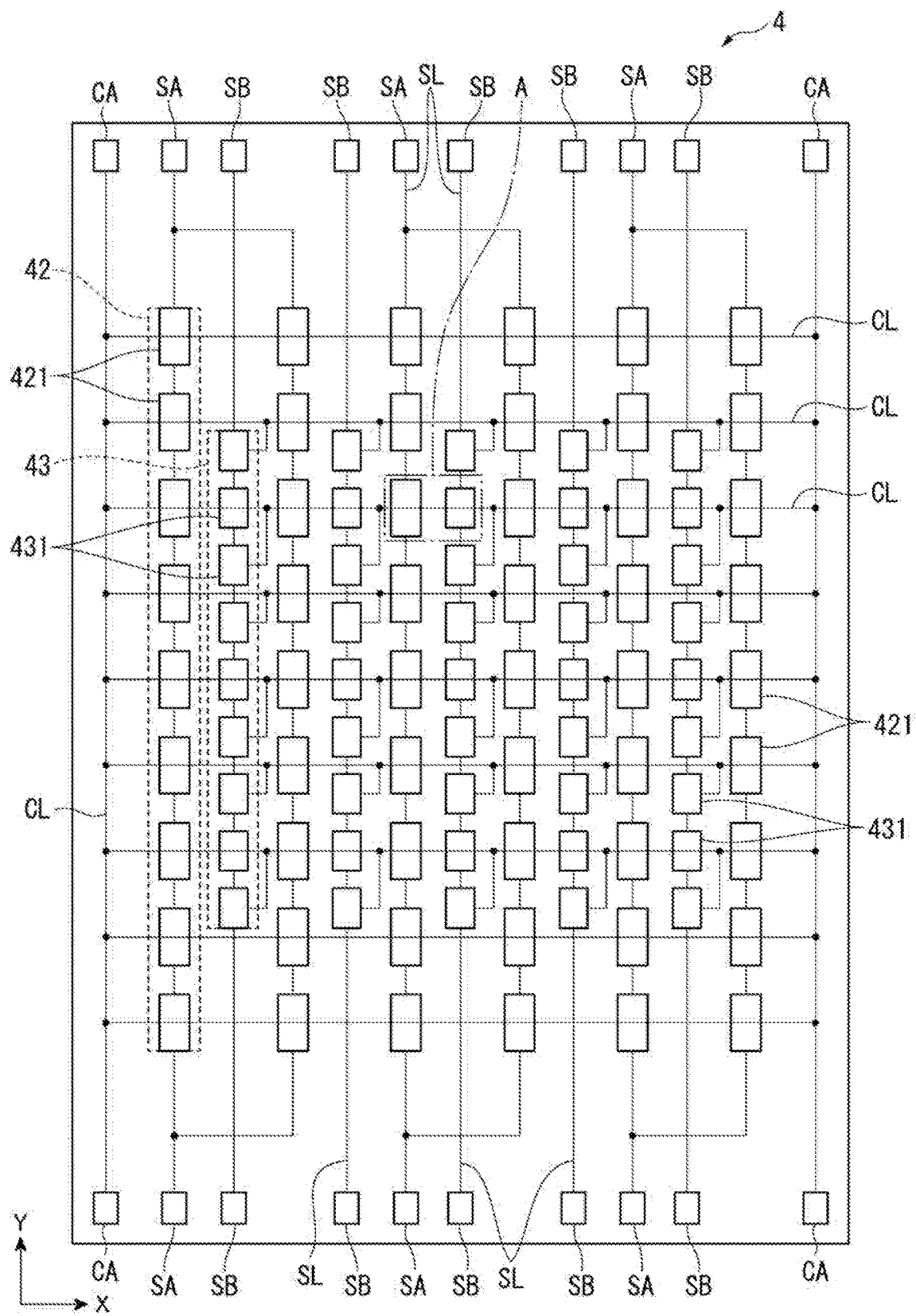
FIG. 4 is a plan view showing a schematic configuration of an ultrasonic device of the first embodiment.

FIG. 4 is a plan view showing an example of the ultrasonic device 4.

In the following description, a scanning direction of the ultrasonic device 4 having a primary array structure as will be described below is referred to as an X direction, and a slice direction intersecting with (for example, in the embodiment, orthogonal to) the scanning direction is referred to as a Y direction.

The ultrasonic device 4 includes an ultrasonic transmitter 42, an ultrasonic receiver 43, a signal electrode line SL, a common electrode line CL, a first signal terminal SA, a second signal terminal SB, and a common terminal CA.

The ultrasonic transmitter 42 has a plurality of transmission transducers 421 which are ultrasonic transducers for transmission, and the plurality of transmission transducers 421 are configured to be disposed in the Y direction. In addition, the ultrasonic receiver 43 has a plurality of reception transducers 431 which are ultrasonic transducers for reception, and the plurality of reception transducers 431 are configured to be disposed in the Y direction.

In the ultrasonic device 4 of the embodiment, the plurality of ultrasonic transmitters 42 and ultrasonic receivers 43 are alternately disposed in the X direction, and one set of ultrasonic transmitters 42 which are adjacent to each other in the X direction function as one transmission channel. In addition, each ultrasonic receiver 43 functions as one reception channel.

Figure 5:
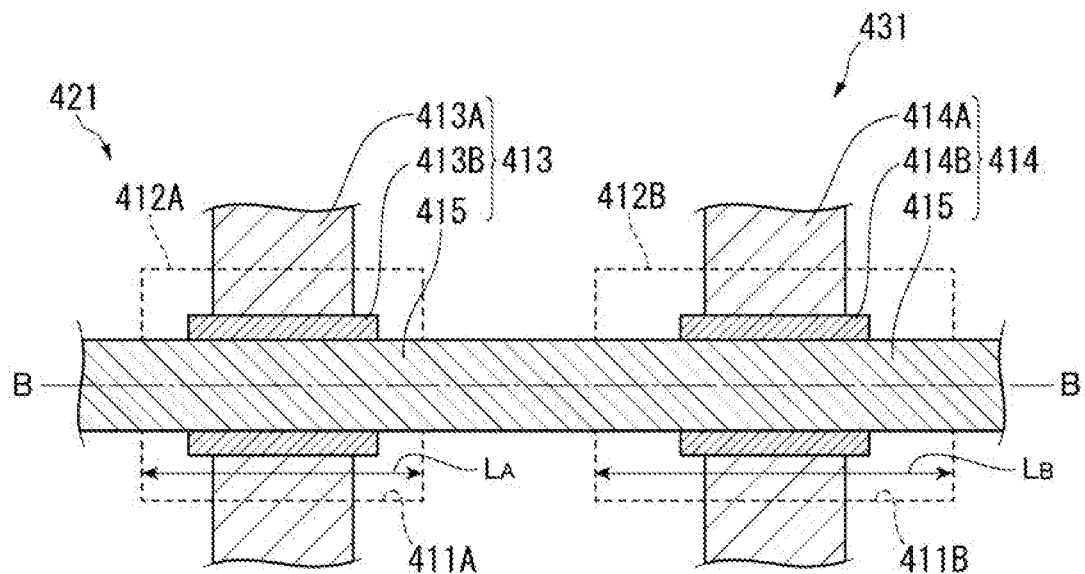
FIG. 5 is an enlarged plan view showing a transmission transducer and a reception transducer by enlarging a part of the ultrasonic device in FIG. 4.
Figure 6:
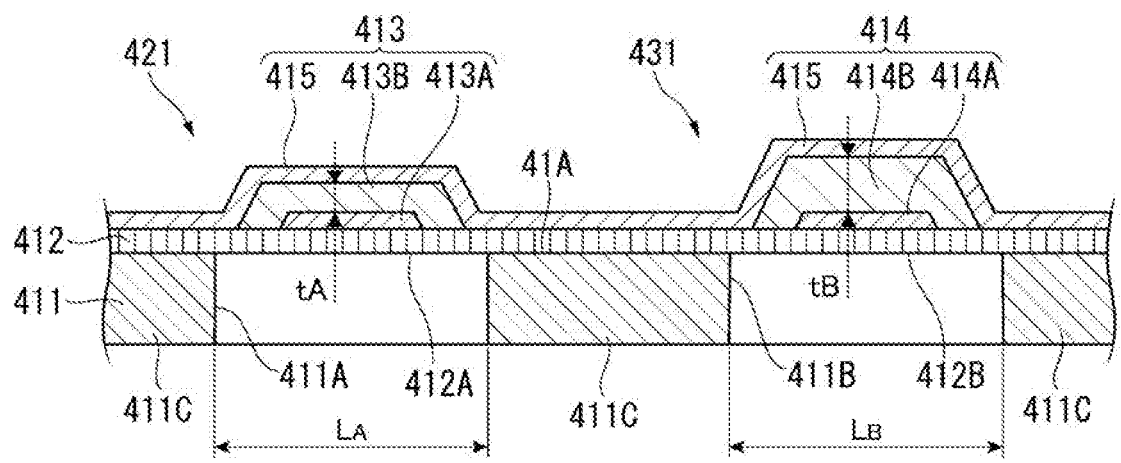
FIG. 6 is a sectional view of the transmission transducer and the reception transducer cut along line B-B in FIG. 5.

FIG. 5 is an enlarged plan view showing the transmission transducer 421 and the reception transducer 431 by enlarging a part (region A shown in FIG. 4) of the ultrasonic device 4 shown in FIG. 4. FIG. 6 is a sectional view showing a section of the transmission transducer 421 and the reception transducer 431 cut along line B-B in FIG. 5.

As shown in FIG. 6, the ultrasonic device 4 includes an element substrate 411, a support film 412 laminated on the element substrate 411, a transmission piezoelectric element 413 provided on the support film 412, and a reception piezoelectric element 414 provided on the support film 412.

For example, the element substrate 411 is a semiconductor substrate made of Si or the like. The element substrate 411 is provided with a first opening 411A provided at a position overlapping a disposed position of each transmission transducer 421 and a second opening 411B provided at a position overlapping a disposed position of each reception transducer 431. The first opening 411A and the second opening 411B are blocked with the support film 412 provided on a side of a back surface 41A of the element substrate 411. Opening widths (opening areas) of the first opening 411A and the second opening 411B will be described below.

A plane orientation of the Si substrate may be any one of (100), (110), or (111). In addition, the element substrate 411 may be configured of a composite substrate of silicon on insulator (SOI) or the like. Further, the element substrate 411 may be made of alumina, $Ga_2O_3$, or GaN.

For example, the support film 412 is configured of a single layer of $SiO_2$, a laminate of $SiO_2$, $ZrO_2$, and yttrium-stabilized zirconium (YSZ), or the like and is provided to cover the side of the entire back surface 41A of the element substrate 411. A thickness dimension of the support film 412 is sufficiently smaller than a thickness dimension of the element substrate 411. Young's modulus of $SiO_2$ is about 75 GPa. In addition, Young's modulus of $ZrO_2$ is about 200 GPa.

Here, as shown in FIGS. 5 and 6, when viewed in the thickness direction of the element substrate 411 and the support film 412, a region of the support film 412 that overlaps the first opening 411A (transmission transducer 421) constitutes a first vibration portion 412A. In addition, as shown in FIGS. 5 and 6, when viewed in the thickness direction of the element substrate 411 and the support film 412, a region of the support film 412 that overlaps the second opening 411B (reception transducer 431) constitutes a second vibration portion 412B. In other words, the first vibration portion 412A is supported by a partition portion 411C that surrounds the first opening 411A, and the second vibration portion 412B is supported by the partition portion 411C that surrounds the second opening 411B.

The transmission piezoelectric element 413 and the first vibration portion 412A that blocks the first opening 411A constitute the transmission transducer 421.

The transmission piezoelectric element 413 is a laminate of a lower electrode 413A, a transmitting piezoelectric film 413B, and an upper electrode 415 and is provided on the first vibration portion 412A.

The lower electrode 413A configures one of a pair of electrodes in which the transmitting piezoelectric film 413B is interposed therebetween in the thickness direction of the element substrate 411, and the upper electrode 415 configures the other of the pair of electrodes.

The lower electrode 413A is formed to have a linear shape in the Y direction and is provided over the plurality of transmission transducers 421. Hence, the lower electrode 413A has the same potential in the transmission transducers 421 aligned in the Y direction. As shown in FIG. 4, the lower electrode 413A is connected to the corresponding first signal terminals SA disposed on the outer peripheral portion of the support film 412 on ±Y sides, by the signal electrode line SL, and is electrically connected to the circuit substrate 6 in the first signal terminal SA.

In the embodiment, two ultrasonic transmitters 42 in the Y direction constitute one set and one transmission channel is formed. Accordingly, as shown in FIG. 5, the two adjacent ultrasonic transmitters 42 are connected to the same first signal terminal SA.

The transmitting piezoelectric film 413B is formed by a thin film of a piezoelectric body made of lead zirconate titanate (PZT) or the like and is configured to cover the lower electrode 413A on the first vibration portion 412A.

The upper electrode 415 is formed to have a linear shape in the X direction and is provided over the plurality of ultrasonic transducers (transmission transducers 421 and reception transducers 431) which are aligned in the X direction. In addition, the upper electrodes 415 are connected to each other by the common electrode line CL, are connected to the common terminals CA provided on the outer peripheral portion (for example, ±Y sides) of the support film 412 (refer to FIG. 4), and are electrically connected to the circuit substrate 6 on the common terminals CA. In other words, in the embodiment, the upper electrode 415 is common to both of the transmission piezoelectric elements 413 and the reception piezoelectric elements 414 aligned in the X direction and is connected to both of the transmission transducers 421 and the reception transducers 431, and the same common potential is applied.

The reception piezoelectric element 414 and the second vibration portion 412B that blocks the second opening 411B constitute the reception transducer 431.

As shown in FIGS. 5 and 6, the reception piezoelectric element 414 is a laminate of a lower electrode 414A, a receiving piezoelectric film 414B, and the upper electrode 415 and is provided on the second vibration portion 412B.

The lower electrode 414A configures one of the pair of electrodes in which the receiving piezoelectric film 414B is interposed therebetween, and the upper electrode 415 configures the other of the pair of electrodes.

Similar to the lower electrode 413A of the transmission piezoelectric element 413, the lower electrode 414A is formed to have a linear shape in the Y direction and is provided over the plurality of reception transducers 431. Hence, the lower electrodes 414A have the same potential in the reception transducers 431 aligned in the Y direction. As shown in FIG. 4, the lower electrode 414A is connected to the corresponding second signal terminals SB disposed on the outer peripheral portion of the support film 412 on ±Y sides, by the signal electrode line SL, and is electrically connected to the circuit substrate 6 in the second signal terminal SB.

Similar to the transmitting piezoelectric film 413B, the receiving piezoelectric film 414B is formed of a thin film of a piezoelectric body made of lead zirconate titanate (PZT) or the like and is configured to cover the lower electrode 414A on the second vibration portion 412B.

It is preferable that the PZT, of which the transmitting piezoelectric film 413B and the receiving piezoelectric film 414B are formed, has a composition ratio of Zr and Ti of 52:48, because a high piezoelectric property is obtained. In addition, when a monoclinic crystal structure is used, it is possible to obtain a higher piezoelectric property. A material of the piezoelectric body is not limited to the PZT and may be a Pb-free material such as $BiFeMnO_3$—$BaTiO_3$ or $KNaNbO_3$. Young's modulus of PZT is about 80 GPa in a thin film.

Values of a piezoelectric constant $e_{ij}$, a relative permittivity $\varepsilon_{ij}$, stiffness $c_{ij}$ of a piezoelectric body PZT used in simulation of this specification employ data of PZT-5H. PZT of the thin film (film formed through sputtering or the like) is known to have substantially the same physical constant as that of PZT of a bulk (relatively large-sized solid cut out from a sintered body).

The lower electrodes 413A and 414A and the upper electrode 415 are preferably made by using a combination of a plurality of materials of Ti, Ir, $TiO_2$, $IrO_2$, and Pt, in terms of conductivity, stability of the materials, and thin film stress to PZT. The lower electrodes 413A and 414A and the upper electrode 415 have the Young's modulus of about 200 GPa.

In the ultrasonic device 4 having such a configuration, a rectangular voltage having a predetermined frequency is applied between the lower electrode 413A and the upper electrode 415, and thereby the first vibration portion 412A is vibrated such that the ultrasonic wave is transmitted from the transmission transducer 421. In addition, when the second vibration portion 412B is vibrated due to the ultrasonic wave reflected from the living body, an output voltage is output from the lower electrode 414A with the receiving piezoelectric film 414B interposed, in response to a strain amount of the receiving piezoelectric film 414B, and the reception of the ultrasonic wave is detected.

In addition, although omitted in the figures, a reinforcing plate is disposed on a side of the support film 412 which is opposite to the element substrate 411. For example, the reinforcing plate is bonded, with a resin layer or the like, to the support film 412 positioned on the partition portion 411C of the element substrate 411 and reinforces the element substrate 411 and the support film 412.

Further, the first opening 411A and the second opening 411B of the element substrate 411 are filled with an acoustic matching layer made of silicone or the like, and the acoustic lens 7 is provided on the acoustic matching layer.

Dimension of Transmission Transducer and Reception Transducer

Next, dimensions of the transmission transducer 421 and the reception transducer 431 described above will be described below.

In the following description, FIGS. 7, 8, and 9 to 18 show results calculated, based on a finite element method by using COMSOL Multiphysics (registered trademark: COMSOL Inc.). In the COMSOL Multiphysics, structure calculation and piezoelectric calculation are performed by being coupled as multiphysics.

Regarding the transmitting sensitivity, a constant voltage 25 V was applied between the upper and lower electrodes, and a displacement amount of a diaphragm, which was obtained in this case, was evaluated. A unit of the transmitting sensitivity is nm. Regarding the receiving sensitivity, a constant hydrostatic pressure was applied to the diaphragm, and a voltage generated between the upper and lower electrodes, which was obtained in this case, was evaluated. A unit of the receiving sensitivity is nV/Pa.

Figure 7:
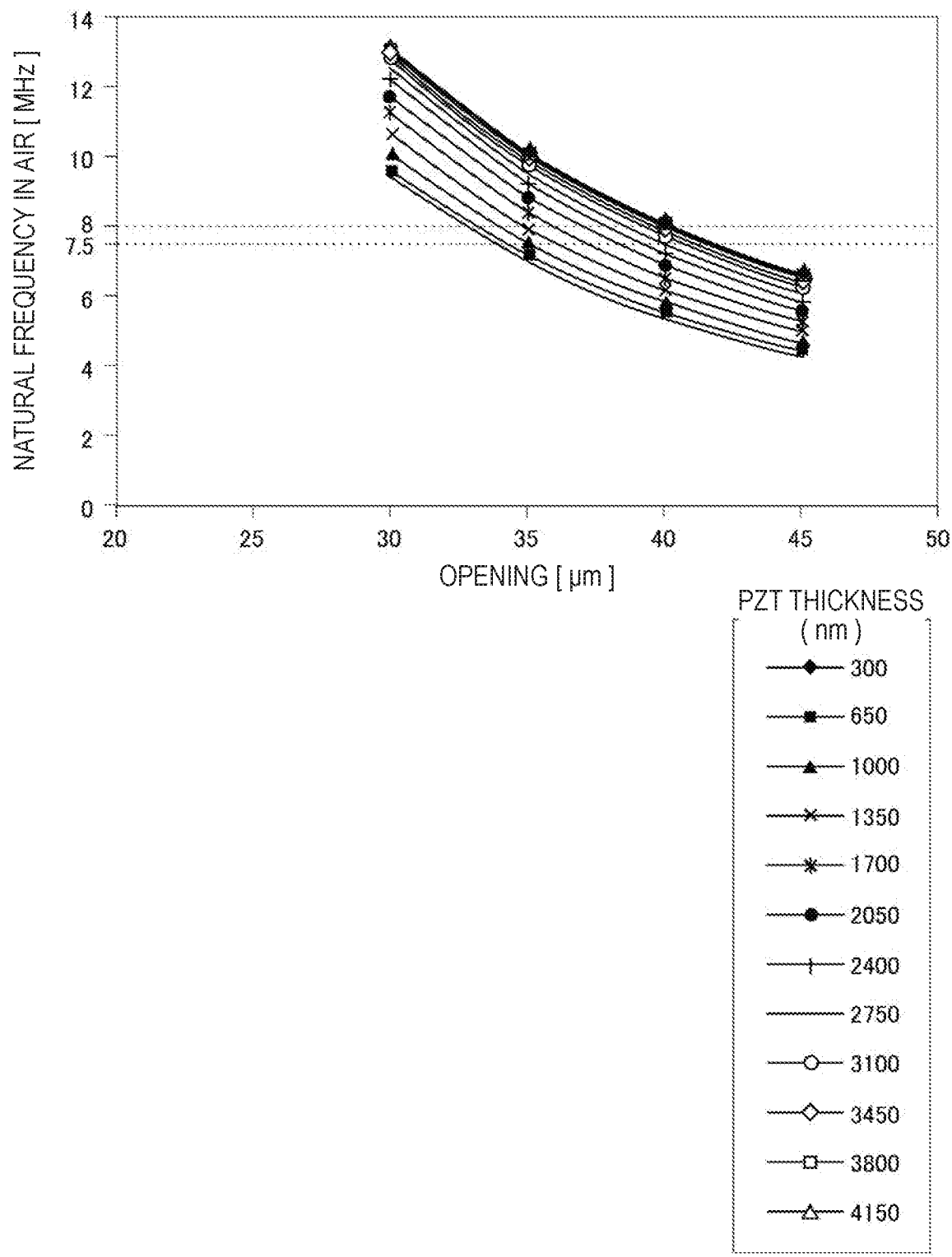
FIG. 7 is a graph showing a relationship between an opening width of an opening of an ultrasonic transducer and a natural frequency of the ultrasonic transducer.

FIG. 7 is a graph showing a relationship between an opening width of an opening (the first opening 411A or the second opening 411B) of the ultrasonic transducer and a natural frequency (frequency of the ultrasonic wave that can be transmitted and received) of the ultrasonic transducer.

In general, the frequency of the ultrasonic wave obtained in a case where the ultrasonic measurement is performed on the living body is about 3 to 14 MHz. As shown in FIG. 7, in a case where ultrasonic waves having frequencies of 3 to 14 MHz described above are received in the ultrasonic transducer (the transmission transducer 421 or the reception transducer 431), the opening width (width dimension in a short axis direction) corresponding to the frequencies is about 30 μm to 45 μm. Hence, in the following description, characteristics of the transmission transducer 421 and the reception transducer 431 obtained in a case where the opening widths of the first opening 411A and the second opening 411B are changed in a range of 30 μm to 45 μm will be described.

Figure 8:
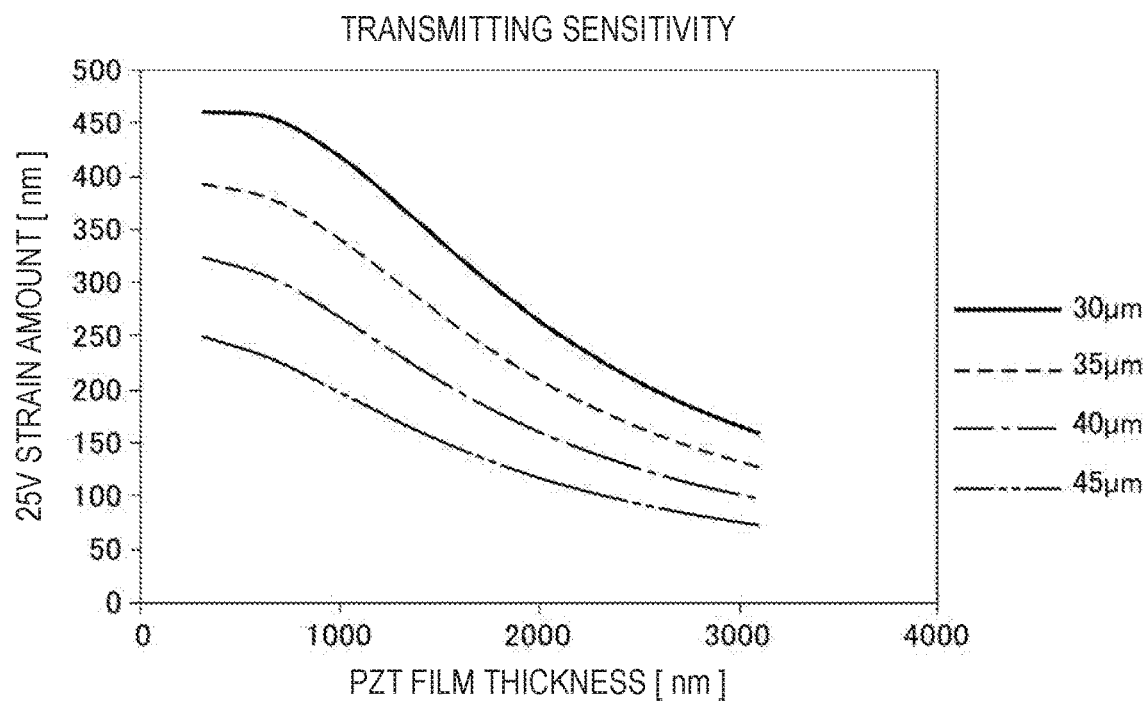
FIG. 8 is a graph showing a relationship between a thickness dimension of a transmitting piezoelectric film and transmitting sensitivity in the transmission transducer.

FIG. 8 is a graph showing a relationship between the thickness dimension of the transmitting piezoelectric film 413B and transmitting sensitivity in the transmission transducer 421. The transmitting sensitivity described here indicates a strain amount (bending amount (nm) in an opening direction, that is, the thickness direction of the support film 412) of the transmitting piezoelectric film 413B obtained when a predetermined drive voltage (for example, 25 V) is applied between the lower electrode 413A and the upper electrode 415.

FIG. 8 is a simulation result obtained through the finite element method. When $t_A$ represents the thickness dimension of the transmitting piezoelectric film 413B, $V_1$ represents a drive voltage that is applied between the lower electrode 413A and the upper electrode 415, $\varepsilon$ represents a dielectric constant of permittivity (the transmitting piezoelectric film) between the electrodes, and e represents a piezoelectric constant of the transmitting piezoelectric film 413B, a strain amount η (transmitting sensitivity) of the transmitting piezoelectric film 413B, which is obtained when the drive voltage $V_1$ is applied, is calculated in a relationship of $\eta = \varepsilon V_1 / t_A e$. The strain amount η (transmitting sensitivity) of the transmitting piezoelectric film 413B, which is obtained when the drive voltage $V_1$ is applied, is obtained through simulation by the finite element method.

Hence, as shown in FIG. 8 the more the thickness dimension $t_A$ increases, the lower the transmitting sensitivity is. Here, it is not preferable that the thickness dimension $t_A$ is smaller than 300 nm, because there is a possibility that dielectric breakdown occurs due to the application of the polarization voltage or the drive voltage during the polarization process.

In addition, in a case where the thickness dimension exceeds 2,750 nm, the first vibration portion 412A is not easily bent due to an influence of the stiffness of the transmitting piezoelectric film 413B (a decrease in the transmitting sensitivity). In particular, in the ultrasonic measuring apparatus 1, the ultrasonic wave transmitted from the transmission transducer 421 is attenuated in the living body, and the reflected ultrasonic wave, which is attenuated, is received by the reception transducer 431. In this case, as the transmitting sensitivity of the transmission transducer 421, the bending amount of the first vibration portion 412A is preferably secured to be larger than at least about 100 nm. In a case where the opening width of the first opening 411A is 30 μm such that the transmitting sensitivity is the lowest level, in order to satisfy the conditions described above, the thickness dimension of the transmitting piezoelectric film 413B is preferably 2,750 nm or smaller.

In other words, in the embodiment, the transmitting piezoelectric film 413B preferably has the thickness dimension $t_A$ in a range of 300 nm or larger and 2,750 nm or smaller.

Figure 9:
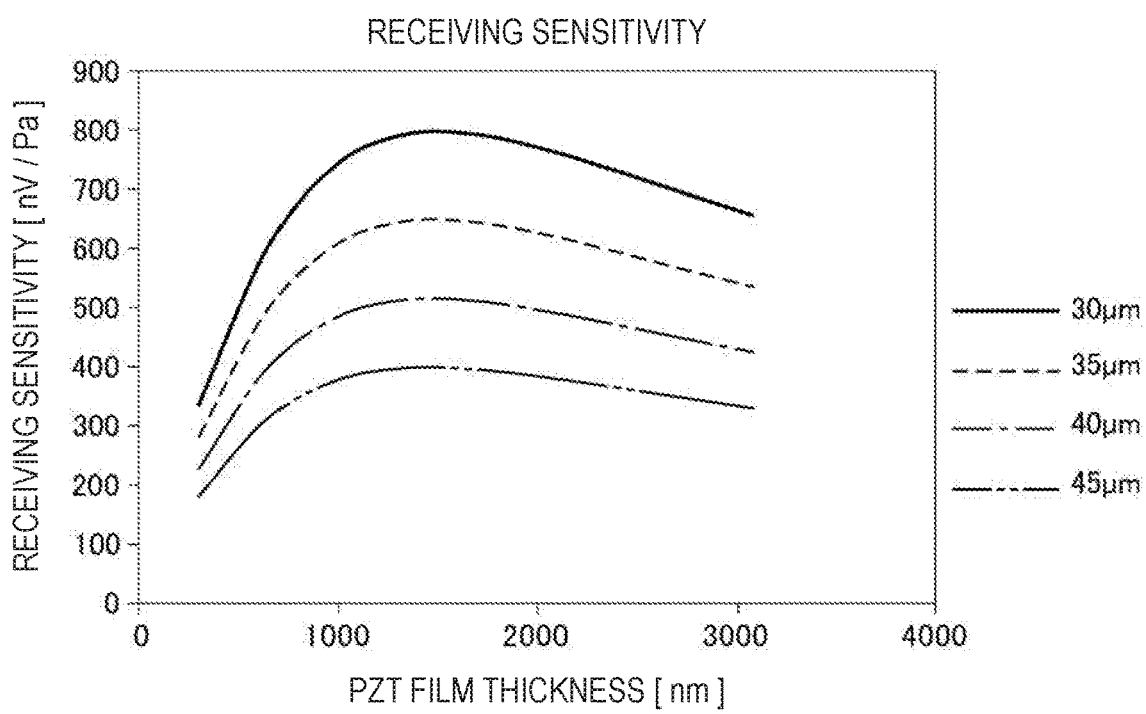
FIG. 9 is a graph showing a relationship between a thickness dimension of a receiving piezoelectric film and receiving sensitivity in the reception transducer.

FIG. 9 shows a relationship between a thickness dimension of the receiving piezoelectric film 414B and receiving sensitivity (nV/Pa) in the reception transducer 431.

When η represents a strain amount of the receiving piezoelectric film 414B, $t_B$ represents the thickness dimension of the receiving piezoelectric film 414B, ε represents a dielectric constant of a permittivity (the transmitting piezoelectric film) between the electrodes, and e represents a piezoelectric constant of the receiving piezoelectric film 414B, an output voltage $V_2$ that is output from the lower electrode 414A in the reception transducer 431 is calculated in a relationship of $V_2 = \eta t_B e/\varepsilon$.

Therefore, when the thickness dimension $t_B$ is larger than 300 nm, the output voltage $V_2$ increases. On the other hand, in a case where the thickness dimension $t_B$ increases too much, the stiffness of the second vibration portion 412B also increases, and thus the second vibration portion is not easily bent. Accordingly, as shown in FIG. 9, regarding the receiving sensitivity of the reception transducer 431, the receiving sensitivity increases as the thickness dimension $t_B$ increases. Then, the receiving sensitivity reaches a peak between 1,300 nm and 1,700 nm, and the receiving sensitivity decreases gradually when the thickness dimension $t_B$ increases more.

Since the reflected ultrasonic wave, which is attenuated, is received in the reception transducer 431, the receiving sensitivity of at least 300 (nV/Pa) or higher is obtained. Here, in a case where the thickness dimension $t_B$ of the receiving piezoelectric film 414B is smaller than 600 nm, it is not possible to satisfy the conditions described above, and thus the receiving efficiency decreases.

In addition, in a case where the thickness dimension $t_B$ is larger than 3,100 nm, the second vibration portion 412B is not easily bent due to an influence of the stiffness of the receiving piezoelectric film 414B, and thus the receiving sensitivity decreases.

In other words, in the embodiment, the receiving piezoelectric film 414B preferably has the thickness dimension $t_B$ in a range of 600 nm or larger and 3,100 nm or smaller.

Incidentally, the ultrasonic device 4 performs the transmission process of the ultrasonic wave by the transmission transducer 421 and performs the reception process of the ultrasonic wave by the reception transducer 431. Therefore, even when only the characteristics of any one process is appropriate, the transmission and reception efficiency decreases in a case where the other is not appropriate.

Here, the inventor of the invention finds that a product of the transmitting sensitivity in the transmission transducer 421 and the receiving sensitivity in the reception transducer 431 is defined as a figure of merit of the transmission/reception process in the ultrasonic device, and, in order to perform the transmission/reception process with high accuracy, the figure of merit needs to be 75,000 or higher.

Figure 10:
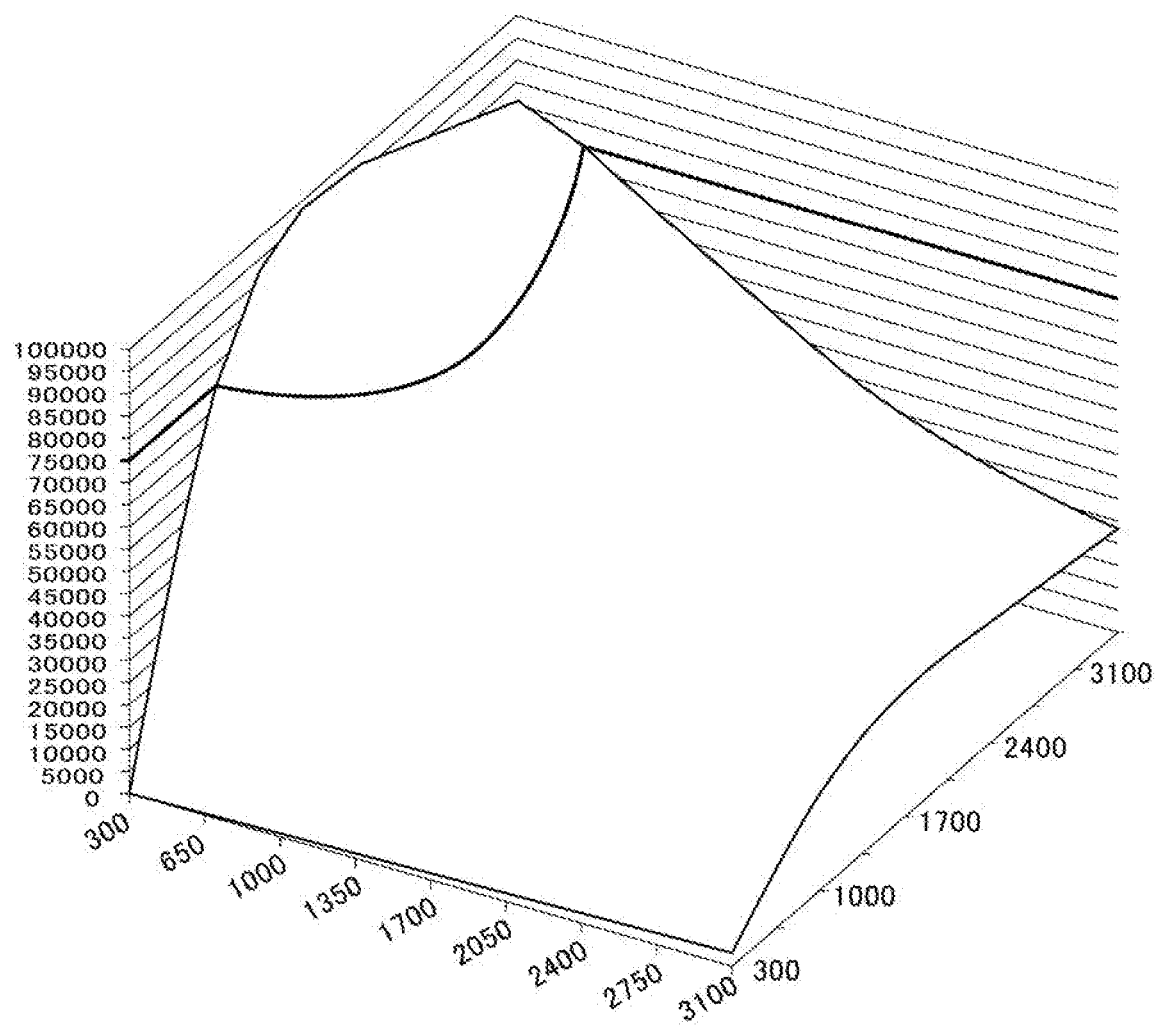
FIG. 10 is a graph showing a relationship between the thickness dimension of the transmitting piezoelectric film, the thickness dimension of the receiving piezoelectric film, and the figure of merit when the first opening and the second opening are 30 μm.
Figure 11:
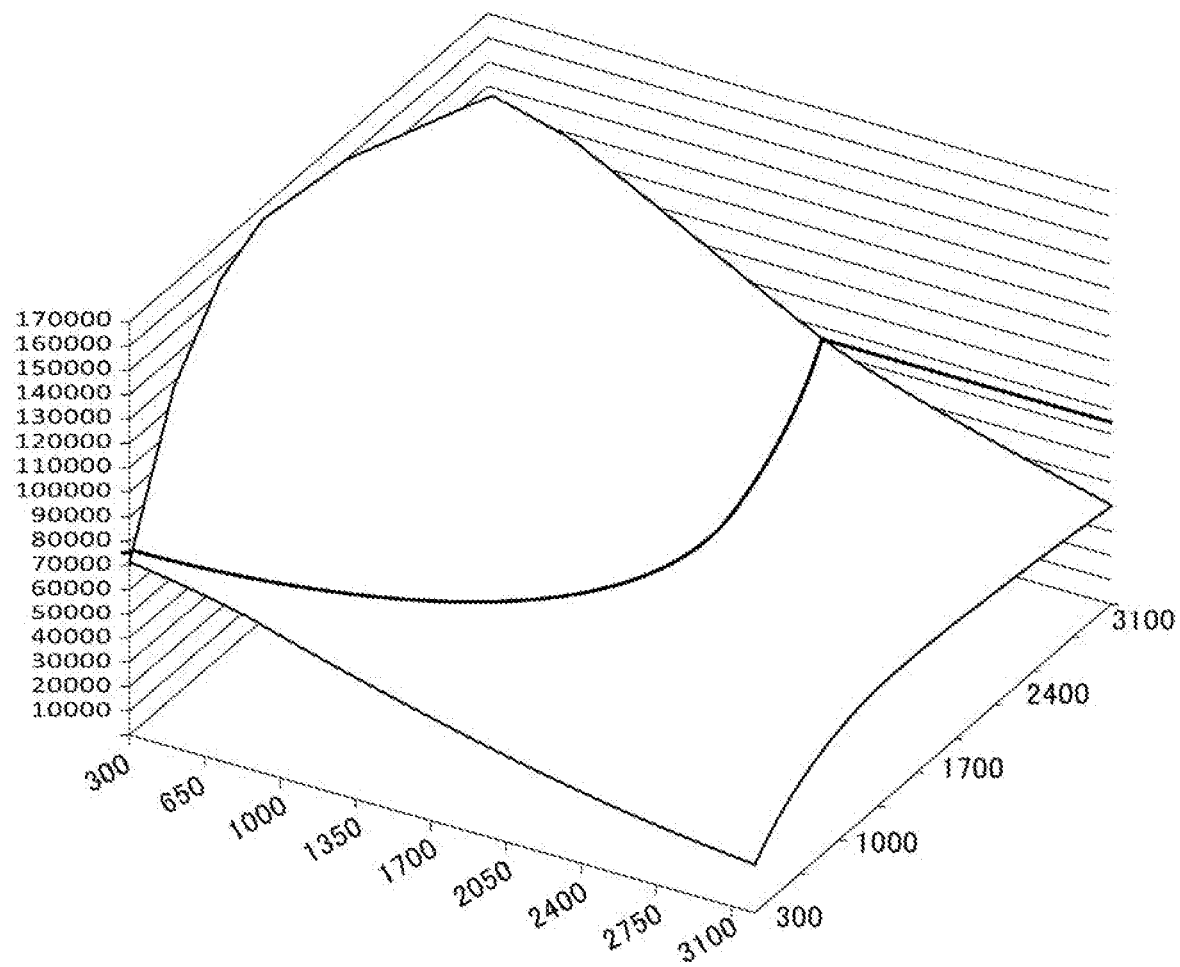
FIG. 11 is a graph showing a relationship between the thickness dimension of the transmitting piezoelectric film, the thickness dimension of the receiving piezoelectric film, and the figure of merit when the first opening and the second opening are 35 μm.
Figure 12:
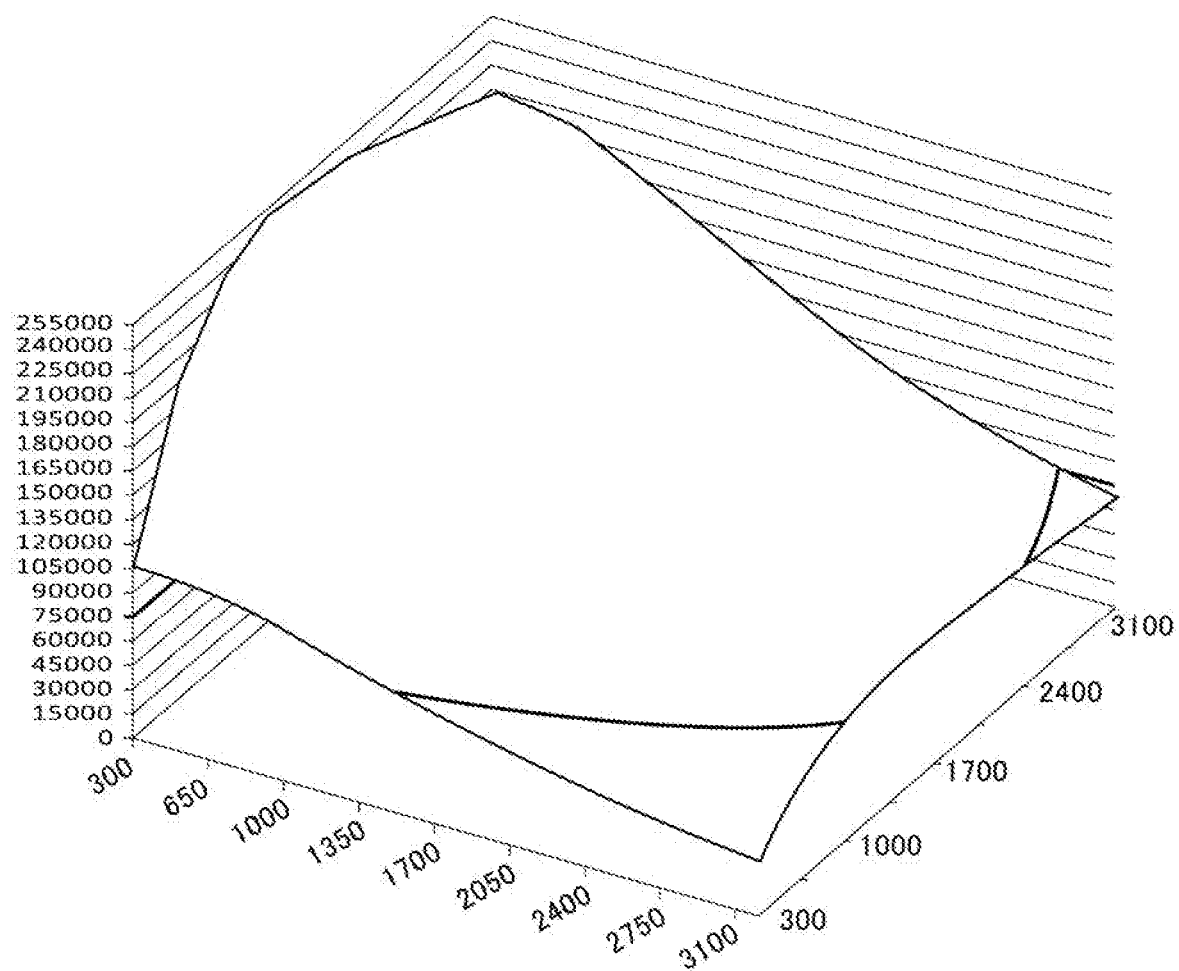
FIG. 12 is a graph showing a relationship between the thickness dimension of the transmitting piezoelectric film, the thickness dimension of the receiving piezoelectric film, and the figure of merit when the first opening and the second opening are 40 μm.
Figure 13:
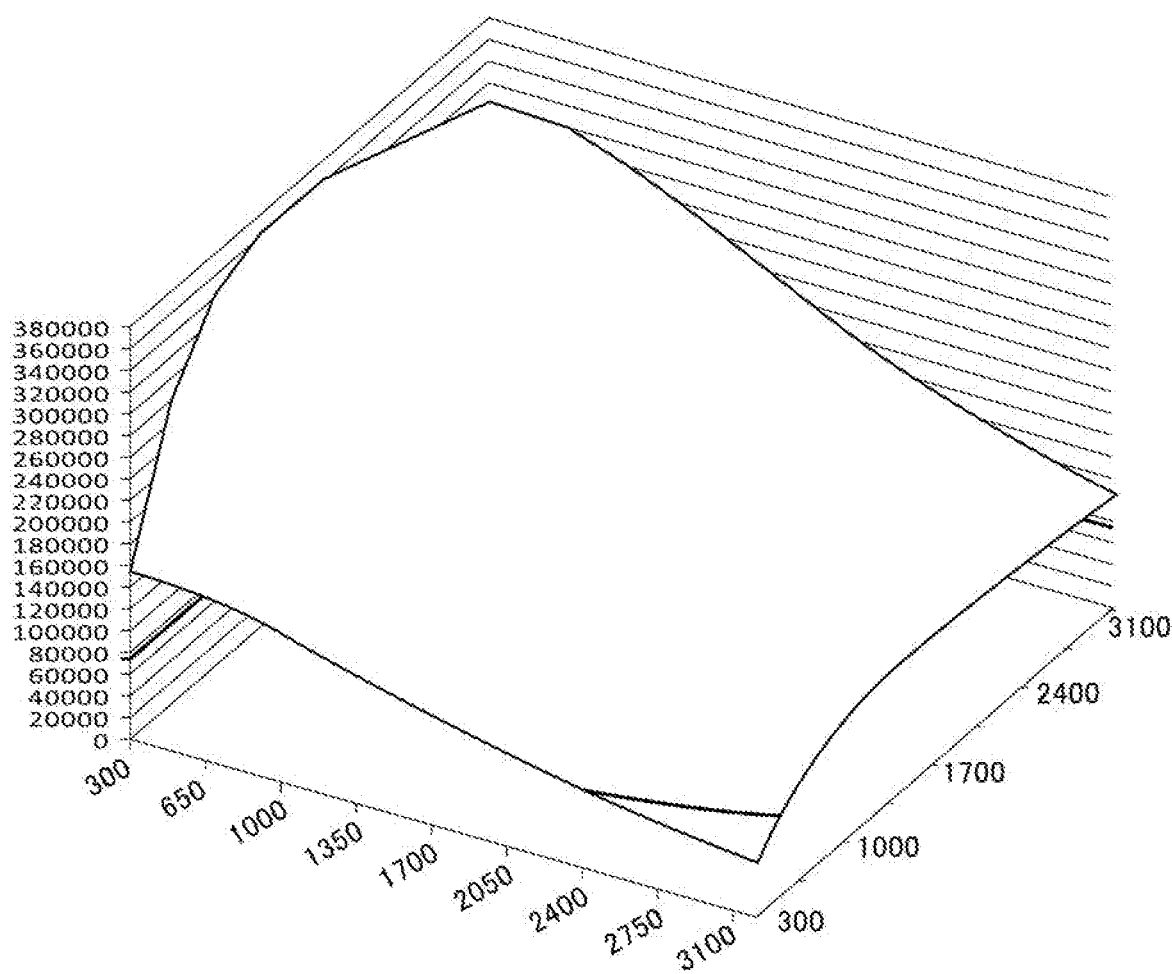
FIG. 13 is a graph showing a relationship between the thickness dimension of the transmitting piezoelectric film, the thickness dimension of the receiving piezoelectric film, and the figure of merit when the first opening and the second opening are 45 μm.

FIG. 10 is a graph showing a relationship between the thickness dimension $t_A$ of the transmitting piezoelectric film 413B, the thickness dimension $t_B$ of the receiving piezoelectric film 414B, and the figure of merit when the first opening 411A and the second opening 411B are 30 μm. FIG. 11 is a graph showing a relationship between the thickness dimension $t_A$ of the transmitting piezoelectric film 413B, the thickness dimension $t_B$ of the receiving piezoelectric film 414B, and the figure of merit when the first opening 411A and the second opening 411B are 35 μm. FIG. 12 is a graph showing a relationship between the thickness dimension $t_A$ of the transmitting piezoelectric film 413B, the thickness dimension $t_B$ of the receiving piezoelectric film 414B, and the figure of merit when the first opening 411A and the second opening 411B are 40 μm. FIG. 13 is a graph showing a relationship between the thickness dimension $t_A$ of the transmitting piezoelectric film 413B, the thickness dimension $t_B$ of the receiving piezoelectric film 414B, and the figure of merit when the first opening 411A and the second opening 411B are 45 μm. In addition, FIGS. 14 to 17 are graphs showing regions in which the figure of merit is 75,000 or higher in FIGS. 10 to 13, respectively. A contour line in FIGS. 10 to 13 is a contour line on which the figure of merit is 75,000.

Figure 18:
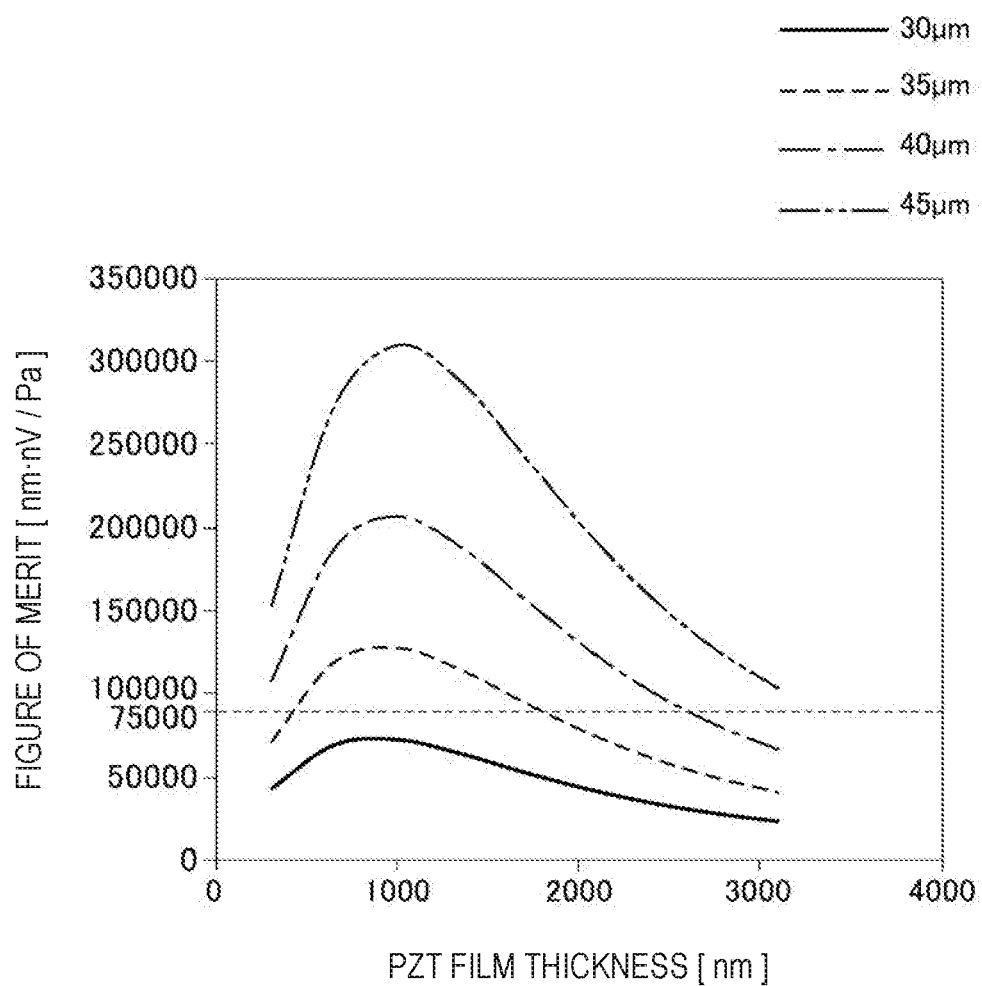
FIG. 18 is a graph showing a figure of merit of an ultrasonic transducer in an example of related art.

In addition, FIG. 18 is a graph showing a figure of merit of the ultrasonic transducer in an example of related art. As the example of the related art, an example in which the transmission and the reception of the ultrasonic wave are performed (the thickness dimension $t_A$ of the transmitting piezoelectric film is the same value as the thickness dimension $t_B$ of the receiving piezoelectric film) by using one ultrasonic transducer is exemplified.

As shown in FIGS. 10 to 18, in the embodiment, the figure of merit increases as the opening widths of the first opening 411A and the second opening 411B increase.

Here, as in the example in the related art, in a case where the thickness dimension $t_A$ of the transmitting piezoelectric film is the same value as the thickness dimension $t_B$ of the receiving piezoelectric film, and the opening widths of the first vibration portion and the second vibration portion are 30 μm, the figure of merit is lower than 75,000. In addition, even in a case where the opening width is 35 μm, a range in which the figure of merit exceeds 75,000 is a range of 400 nm to 1,800 nm in a film thickness of the piezoelectric film, and thus freedom of design decreases.

Figure 14:
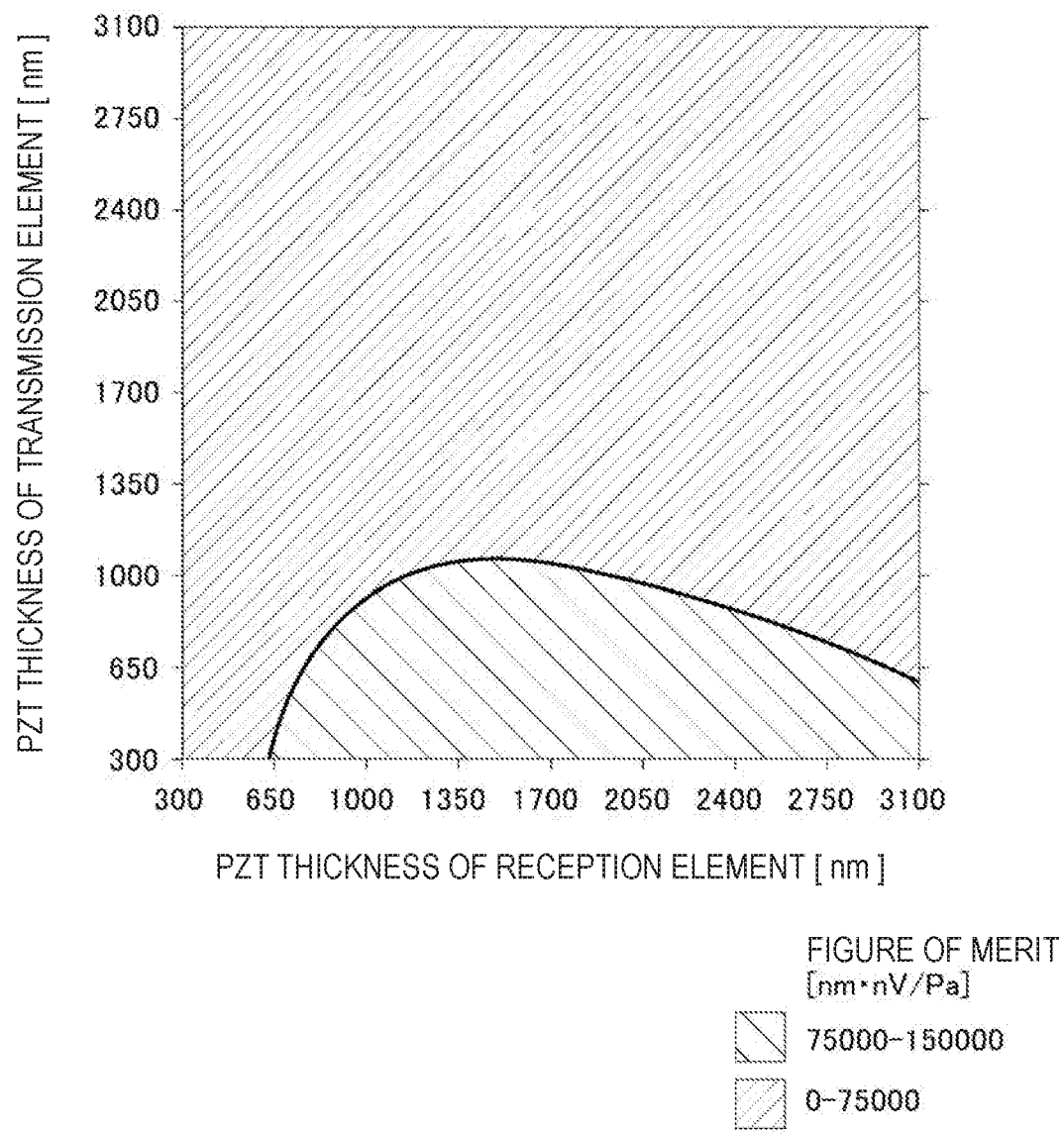
FIG. 14 is a graph showing a region in which the figure of merit is 75,000 or higher from FIG. 10.
Figure 15:
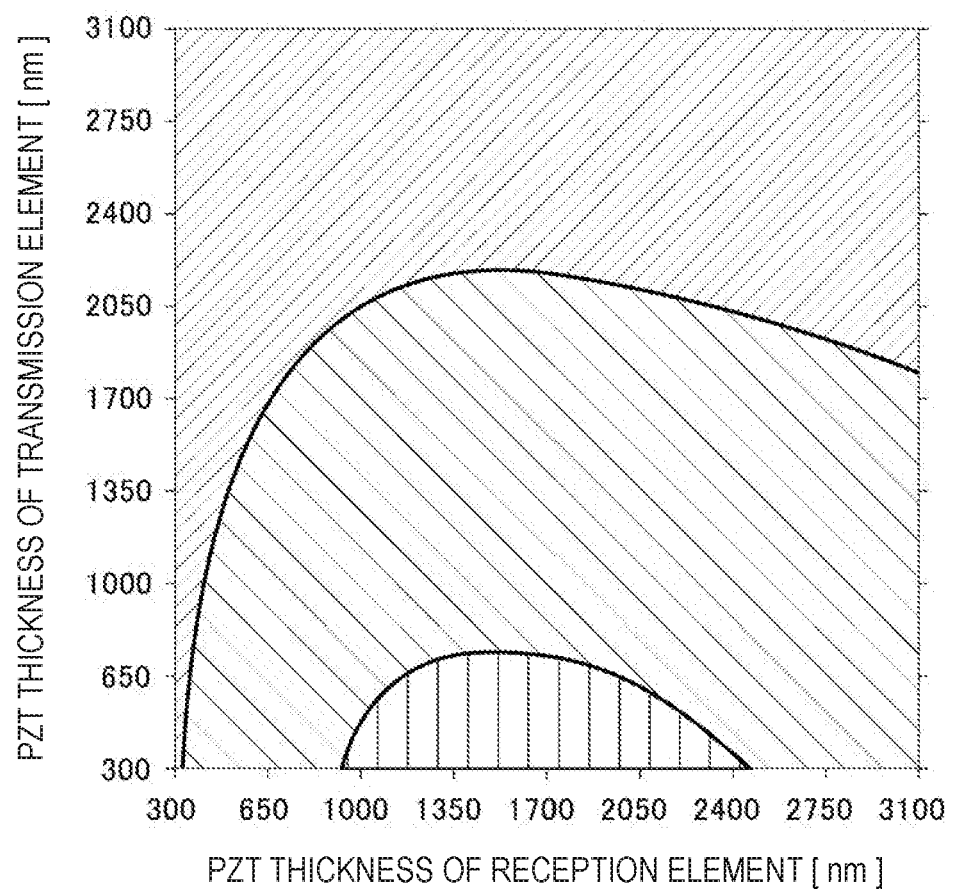
FIG. 15 is a graph showing a region in which the figure of merit is 75,000 or higher from FIG. 11.
Figure 16:
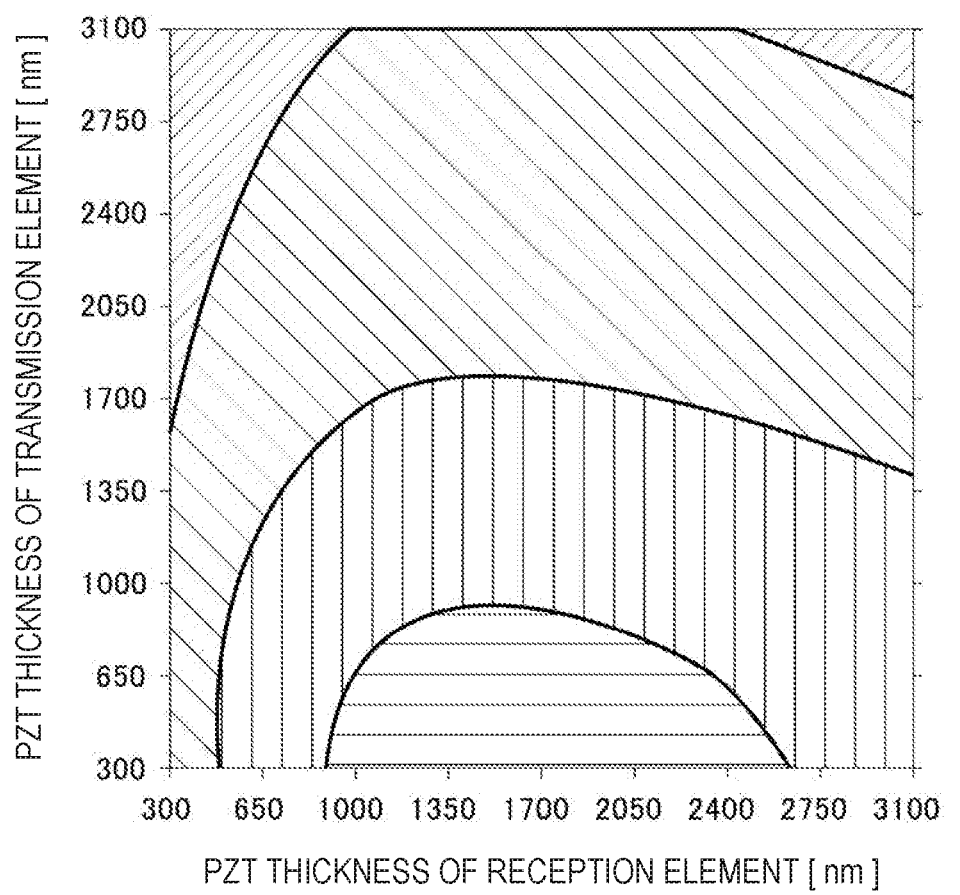
FIG. 16 is a graph showing a region in which the figure of merit is 75,000 or higher from FIG. 12.

By comparison, as shown in FIGS. 10 and 14, in the embodiment, even when the opening widths of the first opening 411A and the second opening 411B are 30 μm, the ultrasonic device 4 having the figure of merit of higher than 75,000 is obtained. For example, in a case where the thickness dimension $t_A$ of the transmitting piezoelectric film 413B is 300 nm such that the maximum transmitting sensitivity is obtained, and the thickness dimension $t_B$ of the receiving piezoelectric film 414B is about 650 nm, the ultrasonic device 4 having the figure of merit of approximately 75,000 is obtained. In addition, in a case where the thickness dimension $t_A$ of the transmitting piezoelectric film 413B is approximately 900 nm, and the thickness dimension $t_B$ of the receiving piezoelectric film 414B is about 650 nm, the ultrasonic device 4 having the figure of merit of approximately 75,000 is obtained. In other words, in a case where the opening widths are 30 μm, the thickness dimension $t_A$ of the transmitting piezoelectric film 413B is in a range of 300 nm or larger and 900 nm or smaller, and the thickness dimension $t_B$ of the receiving piezoelectric film 414B is larger than the thickness dimension $t_A$ by 350 nm or larger, the ultrasonic device 4 having the figure of merit of 75,000 or higher is obtained.

In addition, in a case where the opening widths of the first opening 411A and the second opening 411B are 35 μm or larger, a range in which the figure of merit is larger than 75,000 further increases, compared to a case where the opening width is 30 μm. In addition, as found by comparing to FIG. 18, it is possible to obtain the figure of merit much higher than that in the example of the related art.

As described above, in FIGS. 10 to 17, the thickness dimension $t_A$ of the transmitting piezoelectric film 413B is 300 nm or larger and 2,750 nm or smaller, the thickness dimension $t_B$ of the receiving piezoelectric film 414B is 600 nm or larger and 3,100 nm or smaller, the thickness dimension of the transmitting piezoelectric film 413B is smaller than that of the receiving piezoelectric film 414B, and it is preferable to satisfy a relationship of $t_B-t_A \geq 350$ (nm).

Incidentally, as shown in FIG. 7, in a case where the natural frequency of the ultrasonic transducer is set to a predetermined value, the more the thickness dimension increases, the higher the natural frequency is, and the more the thickness dimension decreases, the lower the natural frequency is, also depending on the thickness dimension of the piezoelectric film (the transmitting piezoelectric film 413B or the receiving piezoelectric film 414B) that constitutes the corresponding ultrasonic transducer.

As described above, the thickness dimension $t_A$ of the transmitting piezoelectric film 413B is smaller than the thickness dimension $t_B$ of the receiving piezoelectric film 414B. In the ultrasonic device 4, in order to perform the transmission/reception process of the ultrasonic wave of the predetermined frequency, the natural frequency of the transmission transducer 421 needs to be substantially the same as the natural frequency of the reception transducer 431. Accordingly, in the embodiment, an opening width $L_A$ of the first opening 411A that overlaps the transmission transducer 421 is formed to be smaller than an opening width $L_B$ of the second opening 411B that overlaps the reception transducer 431.

For example, in a case where the thickness dimension to of the transmitting piezoelectric film 413B is 300 nm, and the thickness dimension $t_B$ of the receiving piezoelectric film 414B is 1,350 nm when the transmission/reception process of the ultrasonic wave having a frequency of 8 MHz is performed, the opening width $L_A$ of the first opening 411A is about 33 μm, and the opening width $L_B$ of the second opening is about 35 μm.

However, when the transmission transducer 421 and the reception transducer 431 have the same value of the natural frequency as each other, and the ultrasonic wave is transmitted from the transmission transducer 421, the reception transducer 431 resonates, and an output voltage in response to the resonance is output from the reception transducer 431 and becomes the noise component.

Hence, in the embodiment, the natural frequency of the transmission transducer 421 is set to a value different from the natural frequency of the reception transducer 431. Specifically, the natural frequency of the reception transducer 431 is set to be smaller, preferably, by a range of 0.2 MHz or higher and 0.8 MHz or lower than the natural frequency of the transmission transducer 421 and is set to be smaller, more preferably, by 0.5 MHz than the natural frequency of the reception transducer 431.

For example, in the transmission/reception process of the ultrasonic wave having the frequency of 8 MHz, in a case where the natural frequency of the transmission transducer 421 is set to 8 MHz, the natural frequency of the reception transducer 431 is set to 7.5 MHz. Hence, in a case where the thickness dimension $t_A$ of the transmitting piezoelectric film 413B is 300 nm, and the thickness dimension $t_B$ of the receiving piezoelectric film 414B is 1,350 nm, the opening width $L_A$ of the first opening 411A is about 33 μm, and the opening width $L_B$ of the second opening 411B is about 37 μm.

In this case, the opening width $L_B$ of the second opening 411B corresponding to the reception transducer 431 increases, the second vibration portion 412B is easily vibrated, and thus the receiving sensitivity is improved.

In the ultrasonic device 4 of the embodiment, a natural frequency $f_A$ of the transmission transducer 421 is set in proportion to a frequency of the ultrasonic wave depending on a measurement site (depth) in the living body and, for example, a frequency smaller than the natural frequency of the transmission transducer 421 by 0.5 MHz is set as a natural frequency $f_B$ of the reception transducer 431. From a combination of the thickness dimension to of the transmitting piezoelectric film 413B that satisfies the natural frequency $f_A$ set above and the opening width $L_A$ of the first opening 411A, and a combination of the thickness dimension $t_B$ of the receiving piezoelectric film 414B that satisfies the natural frequency $f_B$ and the opening width $L_B$ of the second opening 411B, a combination in which the figure of merit is higher than 75,000 in the transmission/reception process of the ultrasonic wave is obtained, and more preferably a combination having the maximum figure of merit is obtained. The transmission transducer 421 and the reception transducer 431 are formed to have the thickness dimension to of the transmitting piezoelectric film 413B, the opening width $L_A$ of the first opening 411A, the thickness dimension $t_B$ of the receiving piezoelectric film 414B, and the opening width $L_B$ of the second opening 411B which are obtained in the manner described above.

Consequently, the ultrasonic device 4 having the optimal transmission and reception efficiency with respect to a desired ultrasonic frequency is configured.

Configuration of Acoustic Lens

Back to FIG. 3, the acoustic lens 7 constituting the ultrasonic sensor 22 is described.

The acoustic lens 7 efficiently propagates, to the living body which is a measurement target, the ultrasonic wave transmitted from the ultrasonic device 4 and efficiently propagates, to the ultrasonic device 4, the ultrasonic wave reflected from the living body. The acoustic lens 7 is disposed along a surface through which the ultrasonic device 4 transmits and receives the ultrasonic wave. Although omitted from the figures, the acoustic matching layer is provided between the ultrasonic device 4 and the acoustic lens 7. The acoustic lens 7 and the acoustic matching layer are made of silicone or the like and have intermediate acoustic impedance set between acoustic impedance of the living body and acoustic impedance of the ultrasonic transducers (the transmission transducer 421 and the reception transducer 431) of the element substrate 411.

Configuration of Circuit Substrate

Next, back to FIG. 2, the circuit substrate 6 will be described.

The circuit substrate 6 is provided with a plurality of drive signal terminals (not shown), a plurality of receiving signal terminals (not shown), and a plurality of common signal terminals (not shown), and the ultrasonic device 4 is connected to the circuit substrate with a wiring member 5. Specifically, each of the plurality of drive signal terminals is connected to the corresponding first signal terminal SA connected to the lower electrode 413A of the transmission transducer 421, and each of the plurality of receiving signal terminals is connected to the corresponding second signal terminal SB connected to the lower electrode 414A of the reception transducer 431. Each of the plurality of common signal terminals is connected to the common terminal CA.

In addition, the circuit substrate 6 is provided with a driver circuit or the like for driving the ultrasonic device 4. Specifically, as shown in FIG. 2, the circuit substrate 6 is configured to have a transmitting circuit 61, a receiving circuit 62, a polarization voltage outputting unit 63, a transmission selecting circuit 64, a reception selecting circuit 65, or the like.

The transmitting circuit 61 outputs, to the transmission selecting circuit 64, the drive voltage having a pulse waveform for driving the transmission transducer 421 under the control of the control device 10.

The receiving circuit 62 outputs, to the control device 10, ab output voltage (receiving signal) output from the reception transducer 431. The receiving circuit 62 is configured to have an amplifier circuit, a low pass filter, an A/D converter, a phase adding circuit, or the like. The receiving circuit converts the receiving signal into a digital signal, removes a noise component, performs amplification to a predetermined signal level, and performs the signal processing such as a phase adding process for each reception channel. Then, the receiving circuit outputs receiving signal after the process to the control device 10.

The polarization voltage outputting unit 63 outputs the polarization voltage for performing the polarization process of the transmitting piezoelectric film 413B and the receiving piezoelectric film 414B.

In order to maintain the transmission and reception efficiency of the transmission transducer 421 and the reception transducer 431, it is necessary to apply an electric field of 200 kV/cm or higher so as to initialize a polarizing direction for both of the transmitting piezoelectric film 413B and the receiving piezoelectric film 414B before the transmission/reception process of the ultrasonic wave is performed (or every certain cycle). In the electric field of lower than 200 kV/cm, the initialization of the polarizing direction of the piezoelectric films is insufficiently performed and the transmission and reception efficiency is reduced.

As described above, the thickness dimension $t_A$ of the transmitting piezoelectric film 413B is smaller than the thickness dimension $t_B$ of the receiving piezoelectric film 414B. Hence, the polarization voltage outputting unit 63 applies a voltage as a reception polarization voltage VB for polarizing the receiving piezoelectric film 414B, the voltage being larger than a transmission polarization voltage VA of polarizing the transmitting piezoelectric film 413B. The following Table 1 shows an example of the thickness dimensions of the piezoelectric films (the transmitting piezoelectric film 413B and the receiving piezoelectric film 414B) and the polarization voltages (the transmission polarization voltage VA and the reception polarization voltage VB) with respect to the thickness dimensions thereof. As shown in Table 1, the polarization voltage outputting unit 63 outputs the transmission polarization voltage VA to the transmission selecting circuit 64 and outputs the reception polarization voltage VB to the reception selecting circuit 65.

TABLE 1

| Transmitting piezoelectric film | | Transmitting piezoelectric film | |
| --- | --- | --- | --- |
| Thickness dimension $t_A$ (nm) | Polarization voltage $V_A$ (V) | Thickness dimension $t_B$ (nm) | Polarization voltage $V_B$ (V) |
| 300 | 6 | 1,350 | 27 |
| 500 | 10 | 1,700 | 34 |
| 800 | 16 | 850 | 17 |

The transmission selecting circuit 64 switches, under the control of the control device 10, between ultrasonic transmitting connection of connecting the ultrasonic transmitters 42 (first signal terminals SA) and the transmitting circuit 61 and transmission polarizing connection of connecting the ultrasonic transmitters 42 (first signal terminals SA) and the polarization voltage outputting unit 63.

The reception selecting circuit 65 switches, under the control of the control device 10, between ultrasonic receiving connection of connecting the ultrasonic receivers 43 (second signal terminals SB) and the receiving circuit 62 and reception polarizing connection of connecting the ultrasonic receivers 43 (second signal terminals SB) and the polarization voltage outputting unit 63.

Configuration of Control Device

As shown in FIG. 2, the control device 10 is configured to include an operating unit 11, a display unit 12, a storage unit 13, and a controller 14. The control device 10 may use, for example, a terminal device such as a tablet terminal, a smartphone, or a personal computer and may be a dedicated terminal device for operating the ultrasonic probe 2.

The operating unit 11 is a user interface (UI) through which a user operates the ultrasonic measuring apparatus 1 and may be formed of a touch panel provided on the display unit 12, operation buttons, a keyboard, a mouse or the like, for example.

The display unit 12 is formed of a liquid crystal display, for example, and displays an image.

The storage unit 13 stores various programs or various pieces of data for controlling the ultrasonic measuring apparatus 1.

For example, the controller 14 is configured to have an arithmetic circuit such as a central processing unit (CPU), a processing circuit that executes processes to be described below, and a storage circuit such as a memory. The controller 14 performs reading of the various programs stored in the storage unit 13, thereby functioning as a transmission/reception control unit 141, a signal processing unit 142, a polarization control unit 143, and the like.

When an operation signal indicating that the ultrasonic measurement is executed is input from the operating unit 11, the transmission/reception control unit 141 causes the transmission selecting circuit 64 to perform switching to the ultrasonic transmitting connection and causes the reception selecting circuit 65 to perform switching to the ultrasonic receiving connection. The transmission/reception control unit 141 outputs the drive voltage from the transmitting circuit 61 and transmits the ultrasonic wave from the transmission transducers 421. In addition, the transmission/reception control unit 141 acquires the receiving signal output from the receiving circuit 62.

The signal processing unit 142 performs a predetermined process based on the receiving signal acquired from the receiving circuit 62. For example, the signal processing unit 142 generates an internal tomographic image of the living body based on the receiving signal and outputs the image to the display unit 12 or performs a measurement process of bloodstream or blood pressure.

For example, the polarization control unit 143 causes the transmission selecting circuit 64 to perform switching to the transmission polarizing connection at a predetermined timing and causes the reception selecting circuit 65 to perform switching to the reception polarizing connection. Examples of the timing include when a power source of the ultrasonic measuring apparatus 1 is switched from an off state to an on state, immediately before the measurement processing is performed by the transmission/reception control unit 141, every certain period, or the like.

Operational Effects of Embodiment

The ultrasonic device 4 of the embodiment includes the transmission transducer 421 and the reception transducer 431. The transmission transducer 421 is configured to have the support film 412 (first vibration portion 412A) that covers the first opening 411A of the element substrate 411 and the transmission piezoelectric element 413 provided on the first vibration portion 412A. The transmission piezoelectric element 413 includes the transmitting piezoelectric film 413B interposed between the lower electrode 413A and the upper electrode 415 in the thickness direction. In addition, the reception transducer 431 is configured to have the support film 412 (second vibration portion 412B) that covers the second opening 411B of the element substrate 411 and the reception piezoelectric element 414 provided on the second vibration portion 412B. The reception piezoelectric element 414 includes the receiving piezoelectric film 414B interposed between the lower electrode 414A and the upper electrode 415 in the thickness direction. In the embodiment, the thickness dimension $t_A$ of the transmitting piezoelectric film 413B is formed to be smaller than the thickness dimension $t_B$ of the receiving piezoelectric film 414B.

In the transmission transducer 421, the smaller the thickness dimension $t_A$ of the transmitting piezoelectric film 413B, the higher the transmitting sensitivity. On the other hand, in the reception transducer 431, the thickness dimension $t_B$ of the receiving piezoelectric film 414B is larger than 300 nm, the receiving sensitivity rapidly increases and reaches its peak when the thickness dimension $t_B$ is 1,300 nm to 1,700 nm. Then, the receiving sensitivity decreases gradually. Hence, the thickness dimension $t_A$ of the transmitting piezoelectric film 413B is smaller than the thickness dimension $t_B$ of the receiving piezoelectric film 414B. In this manner, compared to a case where the transmission and the reception of the ultrasonic wave are performed by one ultrasonic transducer or a case of using the piezoelectric films having the same thickness dimension in the transmission transducer and the reception transducer, it is possible for the transmission transducer 421 to have high transmission efficiency of the ultrasonic wave and it is possible for the reception transducer 431 to have high reception efficiency of the ultrasonic wave.

In addition, in the embodiment, the thickness dimension $t_A$ of the transmitting piezoelectric film 413B is 300 nm or larger and 2,750 nm or smaller, the thickness dimension $t_B$ of the receiving piezoelectric film 414B is 600 nm or larger and 3,100 nm or smaller, and a relationship of $t_B-t_A \geq 350$ nm is obtained. In such a configuration, as shown in FIGS. 10 to 18, the figure of merit (nm·nV/Pa) of the transmission and reception of the ultrasonic wave is larger than 75,000 (nm·nV/Pa) in the ultrasonic device 4, and thus it is possible to obtain the ultrasonic device having the high transmission and reception efficiency.

In the application example, the opening width $L_A$ of the first opening 411A is smaller than the opening width $L_B$ of the second opening 411B. The natural frequency of the transmission transducer 421 or the reception transducer 431 depends on the opening width $L_A$ of the first opening 411A or the opening width $L_B$ of the second opening 411B and the thickness dimension $t_A$ of the transmitting piezoelectric film 413B or the thickness dimension $t_B$ of the receiving piezoelectric film 414B. The natural frequency decreases as the opening width $L_A$ or $L_B$ increases or the thickness dimension $t_A$ or $t_B$ decreases. In the embodiment, the thickness dimension $t_A$ of the transmitting piezoelectric film 413B is smaller than the thickness dimension $t_B$ of the receiving piezoelectric film 414B. Hence, the opening width $L_A$ of the first opening 411A is smaller than the opening width $L_B$ of the second opening 411B, and thereby the frequency of the ultrasonic wave that is transmitted from the transmission transducer 421 can be substantially equal to the frequency of the ultrasonic wave that is received by the reception transducer 431.

In the embodiment, the natural frequency $f_A$ of the transmission transducer 421 is set to be larger than the natural frequency $f_B$ of the reception transducer 431 by 0.2 MHz to 0.8 MHz (more preferably, 0.5 MHz).

When the transmission transducer 421 and the reception transducer 431 have the equal natural frequency to each other, and the ultrasonic wave is transmitted from the transmission transducer 421, the reception transducer 431 resonates, and an output voltage containing the noise component is output and has an influence on the reception accuracy of the ultrasonic sounds. By comparison, in the embodiment, since the natural frequencies of the transmission transducer 421 and the reception transducer 431 are different from each other, it is possible to reduce the noise due to such a resonance, and it is possible to improve the reception accuracy.

Here, in a case where $f_A-f_B<0.2$ MHz is satisfied, it is not possible to sufficiently control the resonance of the reception transducer 431 during the transmission of the ultrasonic wave, and thus the reception accuracy is reduced. In addition, in a case where $f_A-f_B>0.8$ MHz is satisfied, a difference between the frequency of the ultrasonic wave transmitted from the transmission transducer 421 and the frequency of the ultrasonic wave that is suitable to be received by the reception transducer 431 increases, and thus the reception accuracy is reduced in the reception transducer. In this respect, in the range described above, while mixture of the noise component into the output voltage, which is output from the reception transducer 431, is suppressed, it is possible for the reception transducer 431 to receive reflected wave of the ultrasonic wave transmitted from the transmission transducer 421 with high reception accuracy, and improvement in the transmission and reception efficiency of the ultrasonic wave is achieved in the ultrasonic device 4.

In addition, the natural frequency $f_B$ of the reception transducer 431 is lower than the natural frequency $f_A$ of the transmission transducer 421. In this case, since the opening width $L_B$ of the second opening 411B in the reception transducer 431 increases, the second vibration portion 412B is easily bent, and the improvement in the receiving sensitivity is achieved in the reception transducer 431.

In the embodiment, the circuit substrate 6 is provided with the polarization voltage outputting unit 63, and the polarization voltage outputting unit 63 applies the transmission polarization voltage VA to the transmitting piezoelectric film 413B and performs the polarization process before the transmission/reception process of the ultrasonic wave is performed in the ultrasonic device 4, and the polarization voltage outputting unit applies the reception polarization voltage VB larger than the transmission polarization voltage VA to the receiving piezoelectric film 414B and performs the polarization process. When the reception polarization voltage VB is applied to the transmitting piezoelectric film 413B, there is a concern that the voltage will be too high and thus the dielectric breakdown will occur in the transmitting piezoelectric film 413B. When the transmission polarization voltage VA is applied to the receiving piezoelectric film 414B, it is not possible for the sufficient polarization process to be performed, and the receiving sensitivity is considered to be reduced. However, in the embodiment, it is possible to apply the optimal polarization voltage to each of the transmitting piezoelectric film 413B and the receiving piezoelectric film 414B, and it is possible to maintain high transmission and reception efficiency in the transmission transducer 421 and the reception transducer 431.

As described above, in the embodiment, since the transmission and reception efficiency is high in the ultrasonic device 4, it is possible to appropriately perform the transmission/reception process of the ultrasonic wave even in a case where the ultrasonic measurement into the living body is performed by using the ultrasonic probe 2. In addition, the control device 10 is capable of performing highly accurate measurement process (for example, generation of the internal tomographic image, measurement of bloodstream or blood pressure, or the like), based on the results from the ultrasonic measurement obtained by the corresponding ultrasonic device 4.

Modification Examples

The invention is not limited to the embodiments described above, and the invention also includes a configuration obtained through modification, improvement, and an appropriate combination of the embodiments in a range in which it is possible to achieve the object of the invention.

In the embodiment described above, the difference between the thickness dimensions of the transmitting piezoelectric film 413B and the receiving piezoelectric film 414B is 350 nm or larger; however, the difference is not limited thereto. For example, as shown in FIG. 14, the thickness dimension to of the transmitting piezoelectric film 413B may be 650 nm, and the thickness dimension $t_B$ of the receiving piezoelectric film 414B may be 800 nm.

In the embodiment, the opening width $L_A$ of the first opening 411A is smaller than the opening width $L_B$ of the second opening 411B; however, the opening width is not limited thereto.

Figure 17:
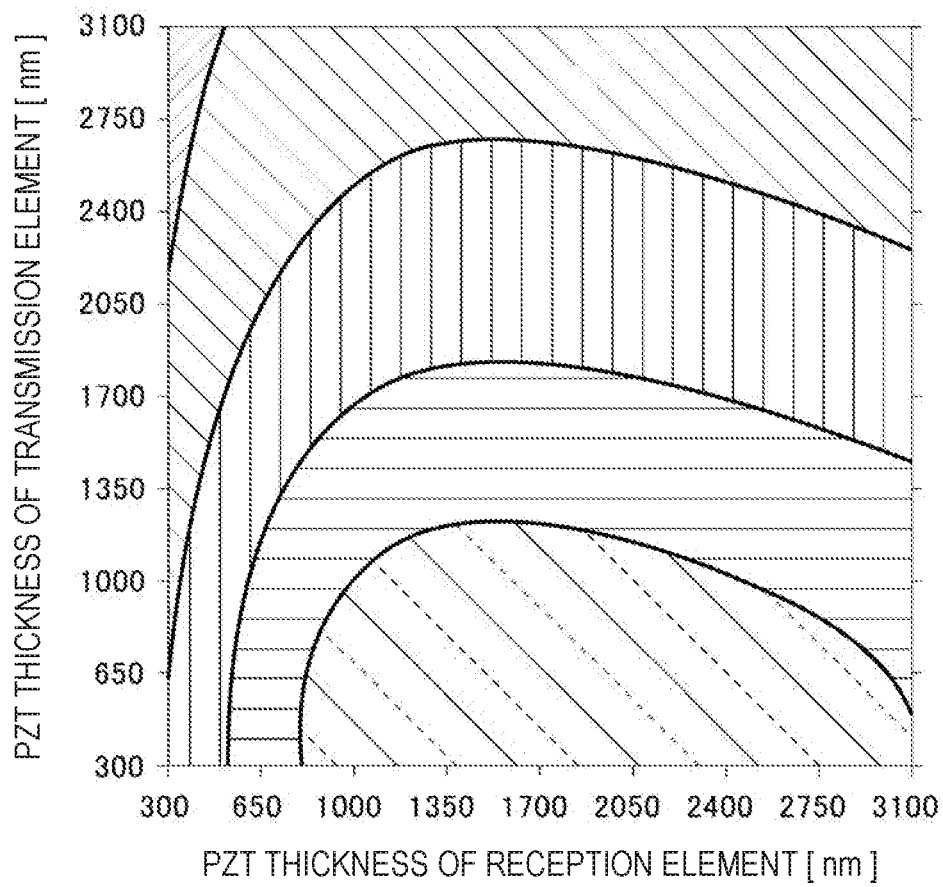
FIG. 17 is a graph showing a region in which the figure of merit is 75,000 or higher from FIG. 13.

As described above, the natural frequency of the transmission transducer 421 is the frequency that is different from the natural frequency of the reception transducer 431, and thereby it is possible to avoid the resonance of the reception transducer 431 during the transmission of the ultrasonic wave. In this case, the natural frequency of the transmission transducer 421 may be smaller than the natural frequency of the reception transducer 431. For example, the natural frequency of the transmission transducer 421 may be 7.5 MHz, and the natural frequency of the reception transducer 431 may be 8 MHz. For example, as shown in FIG. 7, the thickness dimension to of the transmitting piezoelectric film 413B may be 800 nm, the thickness dimension $t_B$ of the receiving piezoelectric film 414B may be 1,300 nm, and the opening widths $L_A$ and $L_B$ of the first opening 411A and the second opening 411B may be 35 μm. In this case, as shown in FIGS. 11 and 17, the figure of merit of the transmission and reception is also a value that is higher than 75,000, and thus it is possible to perform the transmission and reception process with high transmission and reception efficiency in the ultrasonic device 4.

In the embodiment, although an example in which the transmission polarization voltage VA is smaller than the reception polarization voltage VB is exemplified, the polarization voltage is not limited thereto. An electric field of 200 kV/cm or higher may be applied as the polarization voltage without an occurrence of the dielectric breakdown in the transmitting piezoelectric film 413B or the receiving piezoelectric film 414B. Hence, in a case where the dielectric breakdown does not occur in the difference obtained when the reception polarization voltage VB is applied to the transmitting piezoelectric film 413B, the reception polarization voltage VB may be applied to the transmitting piezoelectric film 413B and the receiving piezoelectric film 414B.

In the embodiment, a configuration in which the first opening 411A and the second opening 411B are configured to have a square shape when viewed in the thickness direction of the element substrate 411 is exemplified; however, the shape is not limited thereto. For example, the opening may be formed in a circular shape or may be formed in a rectangular shape.

In the embodiment described above, a configurational example, in which the ultrasonic device 4 transmits the ultrasonic wave to the first opening 411A of the element substrate 411, and the ultrasonic wave that is incident from the second opening 411B is received, is exemplified; however, the invention is not limited thereto. For example, a configuration, in which a reinforcing plate (omitted in the figures) is provided on the element substrate 411 on the opposite side to the support film 412, the ultrasonic wave is transmitted to the opposite side to the first opening 411A (the side of the transmission piezoelectric element 413), and the ultrasonic wave that is incident from the opposite side (the side of the reception piezoelectric element 414) to the second opening 411B, may be employed.

In the embodiment described above, the ultrasonic measuring apparatus that measures a part of the living body as a measurement target is exemplified; however, the invention is not limited thereto. For example, the invention can be applied to an ultrasonic measuring apparatus that detects a defect and checks for aging of a structure, with various type of structures as the measurement target. In addition, the invention can be also applied to an ultrasonic measuring apparatus that detects a defect of a measurement target, with a semiconductor package, a wafer, or the like as the measurement target.

A specific structure when the present invention is implemented may be configured by appropriately combining the respective embodiments and modification examples and may be appropriately changed to other structures or the like within the scope in which it is possible to achieve the object of the present invention.

The invention claimed is:
1. An ultrasonic device comprising:
   a substrate provided with a first opening and a second opening;
   a support film that is provided on the substrate and blocks the first opening and the second opening;

a transmitting piezoelectric film that is provided on the support film at a position which overlaps the first opening when viewed in a thickness direction of the substrate and is interposed between a pair of electrodes in the thickness direction of the substrate; and a receiving piezoelectric film that is provided on the support film at a position which overlaps the second opening when viewed in the thickness direction of the substrate and is interposed between a pair of electrodes in the thickness direction of the substrate, wherein, in the thickness direction of the substrate, a thickness dimension of the transmitting piezoelectric film is smaller than a thickness dimension of the receiving piezoelectric film, and wherein an opening width of the first opening is smaller than an opening width of the second opening.

2. The ultrasonic device according to claim 1, wherein the thickness dimension of the transmitting piezoelectric film is 300 nm or larger and 2,750 nm or smaller, wherein the thickness dimension of the receiving piezoelectric film is 600 nm or larger and 3,100 nm or smaller, and wherein a difference between the thickness dimensions of the transmitting piezoelectric film and the receiving piezoelectric film is 350 nm or larger.

3. The ultrasonic device according to claim 1, wherein the support film is provided with a first vibration portion that blocks the first opening and a second vibration portion that blocks the second opening, wherein a transmission transducer is configured to have the first vibration portion and the transmitting piezoelectric film, wherein a reception transducer is configured to have the second vibration portion and the receiving piezoelectric film, and wherein a natural frequency of the transmission transducer is different from a natural frequency of the reception transducer.

4. The ultrasonic device according to claim 3, wherein a difference between the natural frequency of the transmission transducer and the natural frequency of the reception transducer is 0.2 MHz or higher and 0.8 MHz or lower.

5. The ultrasonic device according to claim 3, wherein the natural frequency of the reception transducer is lower than the natural frequency of the transmission transducer.

6. The ultrasonic device according to claim 1, further comprising:

a polarization voltage output unit that applies a transmission polarization voltage to the transmitting piezoelectric film and applies a reception polarization voltage to the receiving piezoelectric film, wherein the transmission polarization voltage is lower than the reception polarization voltage.

7. An ultrasonic module comprising:

an ultrasonic device including a substrate provided with a first opening and a second opening, a support film that is provided on the substrate and blocks the first opening and the second opening, a transmitting piezoelectric film that is provided on the support film at a position which overlaps the first opening when viewed in a thickness direction of the substrate and is interposed between a pair of electrodes in the thickness direction of the substrate, and a receiving piezoelectric film that is provided on the support film at a position which overlaps the second opening when viewed in the thickness direction of the substrate and is interposed between a pair of electrodes in the thickness direction of the substrate; and a case that stores the ultrasonic device, wherein, in the thickness direction of the substrate, a thickness dimension of the transmitting piezoelectric film is smaller than a thickness dimension of the receiving piezoelectric film, and wherein an opening width of the first opening is smaller than an opening width of the second opening.

8. An ultrasonic measuring apparatus comprising:

an ultrasonic device including a substrate provided with a first opening and a second opening, a transmitting piezoelectric film that is provided on a support film at a position which overlaps the first opening when viewed in a thickness direction of the substrate and is interposed between a pair of electrodes in the thickness direction of the substrate, and a receiving piezoelectric film that is provided on the support film at a position which overlaps the second opening when viewed in the thickness direction of the substrate and is interposed between a pair of electrodes in the thickness direction of the substrate; and a controller that controls the ultrasonic device, wherein, in the thickness direction of the substrate, a thickness dimension of the transmitting piezoelectric film is smaller than a thickness dimension of the receiving piezoelectric film, and wherein an opening width of the first opening is smaller than an opening width of the second opening.

* * * * *